US012808370B2

(12) United States Patent
Houssiere et al.

(10) Patent No.: US 12,808,370 B2
(45) Date of Patent: Nov. 24, 2026

(54) SYSTEMS, DEVICES, AND METHODS FOR CONTROLLED FLUID DELIVERY

(71) Applicant: Bayou Surgical, Inc., Houston, TX (US)

(72) Inventors: Charles Houssiere, Houston, TX (US); Joshua Corso, Houston, TX (US); Scott Sloss, Houston, TX (US); Abdul Umaru, Houston, TX (US); Jorge Salazar, Houston, TX (US); William E. Cohn, Bellaire, TX (US); Rajitha Aluru, Houston, TX (US)

(73) Assignee: Bayou Surgical, Inc., Houston, TX (US)

( * ) Notice: Subject to any disclaimer, the term of this patent is extended or adjusted under 35 U.S.C. 154(b) by 0 days.

(21) Appl. No.: 18/885,490

(22) Filed: Sep. 13, 2024

(65) Prior Publication Data

US 2025/0003402 A1 Jan. 2, 2025

Related U.S. Application Data

(63) Continuation of application No. PCT/US2023/064451, filed on Mar. 15, 2023.

(Continued)

(51) Int. Cl.

*F04B 43/08* (2006.01)
*F04B 13/00* (2006.01)

(Continued)

(52) U.S. Cl.

CPC .............. *F04B 43/08* (2013.01); *F04B 13/00* (2013.01); *F04B 53/10* (2013.01); *A61B 1/126* (2013.01)

(58) Field of Classification Search

CPC ...... A61B 1/126; A61B 1/00119; F04B 43/08
See application file for complete search history.

(56) References Cited

U.S. PATENT DOCUMENTS 4,411,652 A * 10/1983 Kramer ............. A61M 5/14224 417/478
5,478,211 A 12/1995 Dominiak et al.

(Continued)

FOREIGN PATENT DOCUMENTS

DE 4222810 A1 1/1993
WO WO-9721030 A1 6/1997

(Continued)

OTHER PUBLICATIONS

International Preliminary Report on Patentability for International Application No. PCT/US2023/064451 mailed Sep. 26, 2024, 8 pages.

(Continued)

*Primary Examiner* — Nicole Gardner
(74) *Attorney, Agent, or Firm* — COOLEY LLP

(57) ABSTRACT

Systems, devices and methods described herein relate to fluid delivery devices and, in particular, fluid delivery devices that are designed to deliver small volumes of liquid. In some embodiments, an apparatus includes a first housing containing a liquid reservoir and a liquid supply line fluidically coupled to the liquid reservoir and to a liquid outlet configured to couple to an instrument. The supply line includes at least one flexible portion, with first and second valves disposed upstream and downstream thereof, such that compression of the flexible portion pumps liquid toward the liquid outlet. The apparatus can further include a second housing defining a receptacle for receiving at least a portion of the first housing and a pump mechanism disposed within the second housing configured to extend toward the first (Continued)

housing to compress the flexible portion when the first housing is received within the receptacle.

18 Claims, 23 Drawing Sheets

Related U.S. Application Data

(60) Provisional application No. 63/320,126, filed on Mar. 15, 2022.

(51) Int. Cl.
*F04B 53/10* (2006.01)
*A61B 1/12* (2006.01)

(56) References Cited

U.S. PATENT DOCUMENTS

| | | | | |
|---|---|---|---|---|
| 5,551,850 A | 9/1996 | Williamson et al. | | |
| 5,749,829 A * | 5/1998 | Yokoi | A61B 1/00068 | 600/153 |
| 7,479,106 B2 * | 1/2009 | Banik | A61B 1/00097 | 600/156 |
| 8,353,860 B2 * | 1/2013 | Boulais | A61B 1/00094 | 604/27 |
| 2012/0172800 A1 | 7/2012 | Dudar et al. | | |
| 2019/0060117 A1 | 2/2019 | Sussman et al. | | |
| 2019/0125176 A1 | 5/2019 | Burt et al. | | |
| 2021/0127963 A1 | 5/2021 | Aluru et al. | | |
| 2021/0127964 A1 | 5/2021 | Aluru et al. | | |

FOREIGN PATENT DOCUMENTS

| | | |
|---|---|---|
| WO | WO-2021170561 A1 | 9/2021 |
| WO | WO-2023178186 A2 | 9/2023 |

OTHER PUBLICATIONS

International Search Report and Written Opinion for International Application No. PCT/US2023/064451, mailed on Aug. 24, 2023, 11 pages.

Invitation to Pay Additional Fees for International Application No. PCT/US2023/064451 dated May 31, 2023, 3 pages.

EP Application No. 23771638.6, Extended European Search Report mailed Jan. 30, 2026; Applicant Bayou Surgical, Inc.; 11 pages.

* cited by examiner

200

650

SYSTEMS, DEVICES, AND METHODS FOR CONTROLLED FLUID DELIVERY

CROSS-REFERENCE TO RELATED APPLICATIONS

This application is a continuation of International Patent Application No. PCT/US2023/064451 filed Mar. 15, 2023, titled "SYSTEMS, DEVICES, AND METHODS FOR CONTROLLED FLUID DELIVERY," which claims priority to U.S. Provisional Patent Application No. 63/320,126, filed Mar. 15, 2022, titled "SYSTEMS, DEVICES, AND METHODS FOR CONTROLLED FLUID DELIVERY," the disclosures of which are hereby incorporated by reference in their entirety.

TECHNICAL FIELD

The present disclosure generally relates to fluid delivery devices and methods thereof, and in particular to fluid delivery devices for supplying small and precise volumes of fluid in an intermittent operation.

BACKGROUND

Many medical applications require delivery of small amounts or volumes of fluid. For example, delivery of small volumes of a liquid may be required for delivery of certain therapeutic agents, such as drugs. Pumps or other types of medical fluid delivery devices can be used for delivery of therapeutic agents. Such fluid delivery devices can provide fluid delivery continuously or intermittently. Delivery of small volumes of liquid can also be useful in non-therapeutic applications, including, for example, cleaning or disinfecting operations. In particular, small volumes of liquid can be useful for cleaning instruments, including endoscopes. For example, U.S. Patent Application Publication No. 2019/0125176 describes an intraoperative endoscope cleaning device that uses liquid and gas to clean the lens of the endoscope.

Delivery of fluid, however, can be challenging when the volumes required are small. With small volumes, it can be challenging to control the precision of the dispensed volume. Multiple factors in the system and its operation can also affect the precision of the fluid delivery.

SUMMARY

Embodiments described herein relate to fluid delivery devices for dispensing small volumes of liquid, and systems and methods thereof. Such fluid delivery devices can be configured to deliver small volumes of fluid on an intermittent basis. In some embodiments, fluid delivery devices described herein can be configured to delivery small volumes of fluid that are less than, for example, 50 μL.

In some embodiments, a fluid delivery device can include a flexible tube having one-way valves disposed at each end. One end of the tube can be a fill end and the other end of the tube can be a supply end. Fluid can be introduced into the flexible tube from the fill end and ejected or dispensed out of the flexible tube from the supply end. The fill end can be connected to a reservoir, and the supply end can be connected to a medical device, such as, for example, a trocar for cleaning a surgical instrument.

In some embodiments, the operation of a fluid delivery system can be controlled in three phases or modes. In a first mode, the system can be in standby, whereby the valves of the system are closed and fluid within the system does not flow. In a second mode, an actuator can operate a pump within the system to compress a flexible tubing. During compression, an upstream valve can prevent back flow of fluid but a downstream valve can open to allow for fluid dispensing. After the compression of the flexible tubing, the system can transition to a third mode, whereby the tubing returns to its original, uncompressed configuration, and fluid fills back into the flexible tubing. During this last mode, the upstream valve can open to allow fluid to flow into the flexible tubing, but the downstream valve can remain closed to prevent fluid from being delivered until the next compression event. During each cycle through the three modes, a fixed volume of fluid can be delivered. The fixed volume of fluid can be defined by the mechanical displacement of the tubing and the internal dimensions of the tubing.

In some embodiments, an apparatus includes: a housing; a liquid reservoir disposed within the housing; a liquid outlet configured to couple to a surgical instrument; a liquid supply line disposed in the housing, the liquid supply line being fluidically coupled to the liquid reservoir and to the liquid outlet, the liquid supply line having at least one portion that is flexible; and first and second valves disposed along the liquid supply line, the first valve being disposed upstream of the at least one flexible portion and the second valve being disposed downstream of the at least one flexible portion, the at least one flexible portion being compressible to pump liquid disposed within the liquid supply line toward the liquid outlet.

In some embodiments, an apparatus includes: an inflow port couplable to a liquid reservoir; an outflow port couplable to a surgical instrument; a flexible liquid channel coupled to the inflow port and the outflow port, the flexible liquid channel configured to be compressed such that liquid within the flexible liquid channel is displaced toward the outflow port; an inflow valve disposed upstream of the flexible liquid channel; and an outflow valve disposed downstream of the flexible liquid channel, the outflow valve configured to open, when the flexible liquid channel is compressed, such that a first volume of liquid can pass through the outflow valve toward the outflow port, and the outflow valve configured to close and the inflow valve configured to open, when the flexible liquid channel transitions back to an uncompressed state after being compressed, such that a second volume of liquid can pass through the inflow valve and into the flexible liquid channel.

In some embodiments, an apparatus includes: a liquid supply line including a liquid inlet that is fluidically coupled to a liquid reservoir and a liquid outlet that is fluidically coupled to an instrument, the liquid supply line having at least one portion that is configured to be compressed to pump liquid disposed within the liquid supply line toward the instrument; a pump mechanism configured to compress the at least portion of the liquid supply line; and a controller operatively coupled to the pump mechanism and to the instrument, the controller configured to: receive a signal from a sensor disposed at the instrument indicating that a device is positioned for cleaning relative to the instrument; in response to receiving the signal from the sensor, activating a wash sequence in which a first volume of liquid is delivered into the instrument to clean the device; and activating the pump mechanism to compress the at least one portion of the liquid supply line to pump a second volume of liquid toward the instrument such that the instrument is primed for a subsequent wash sequence.

In some embodiments, a system includes: a housing defining a receptacle; an instrument including a distal end configured to be disposed within a patient body; a connector including a first end configured to be received within the receptacle and a second end configured to couple to the instrument, the connector including: a liquid reservoir containing a liquid; and a liquid supply line fluidically coupled to the liquid reservoir, the liquid supply line configured to deliver the liquid to the instrument when the connector is coupled to the instrument, the liquid supply line having at least one portion that is flexible; and a pump mechanism disposed within the housing, the pump mechanism configured to compress the at least one flexible portion to pump the liquid toward the instrument when the connector is received within the receptacle.

In some embodiments, a method includes: actuating a pump mechanism to compress a flexible liquid channel by a predetermined amount; in response to the actuation of the pump mechanism, opening a first valve located downstream from the flexible liquid channel such that a first fixed volume of liquid can pass through the first valve toward an instrument; retracting the pump mechanism to allow the flexible liquid channel to transition back to an uncompressed state; and in response to the flexible liquid channel transitioning back to the uncompressed state, closing the first valve and opening a second valve located upstream from the flexible liquid channel such that a second fixed volume of liquid can pass through the second valve into the flexible liquid channel.

BRIEF DESCRIPTION OF DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements). Also in the drawings, optional items are shown in dashed lines.

DETAILED DESCRIPTION

Figure 1:
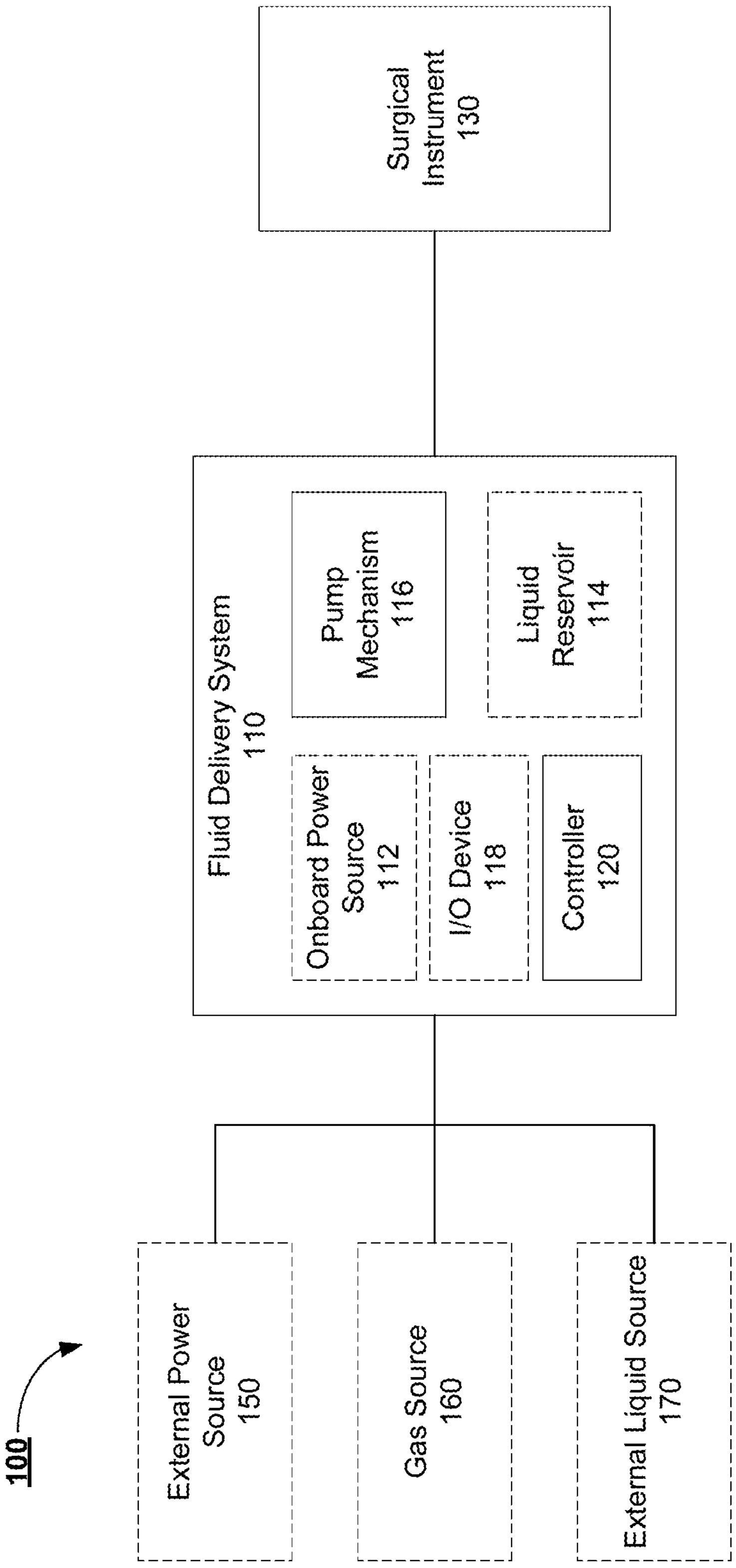
FIG. 1 is a block diagram of a system for delivering liquid and/or gas to a surgical instrument, according to an embodiment.

Described herein are systems, devices, and methods for delivering fluid. In some embodiments, the systems, devices, and methods described herein may be configured to deliver predetermined amounts of fluid on an intermittent basis.

In some embodiments, the fluid delivery systems and devices described in this disclosure are designed to deliver fluid to a medical instrument (e.g., a surgical instrument) or deliver fluids to a patient (e.g., via an intravenous therapy (IV), directly into a cavity of a patient's body via a catheter, or through a nasal or oral passages). The fluid delivery systems and devices are designed to deliver prescribed small amounts of fluid to the medical instrument or to the body of the patient. The delivered fluid may be a liquid, such as, for example, a therapeutic agent, a drug, a biological fluid, a wash or cleaning solution, etc.

In some embodiments, the fluid delivery systems and devices described herein can form part of systems for cleaning medical devices, such as, for example, surgical instruments or imaging devices (e.g., endoscopes). The cleaning systems can be configured to clean the instruments while the instruments are positioned within patient anatomy (e.g., a body lumen or cavity), e.g., when they are in use during a surgical procedure. The fluid delivery systems or devices can supply small, controlled amounts of liquid for cleaning or washing the surgical instruments. The liquid can include a wash solution for cleaning the surgical instrument. In some embodiments, the fluid delivery systems can also supply a gas. The gas can include carbon dioxide ($CO_2$), air, nitrogen, argon, or any other suitable inert gas or combinations thereof. In some embodiments, the gas can be used to expel the liquid, e.g., in a wash operation associated with cleaning an instrument.

In various embodiments, the instrument being cleaned can be an endoscope that is positioned within a body lumen or cavity. The endoscope can be configured to use light (e.g., a visible or an infrared light) to provide visualization of the inside of a body cavity. The endoscope can be positioned within a trocar that can be equipped fluid delivery port(s) for delivering liquid and/or gas for cleaning the endoscope. In use, the endoscope can be retracted within the trocar, and a bolus or small volume of liquid (e.g., wash solution) can be ejected from the fluid delivery port(s) to clean the endoscope. Systems, devices, and methods described herein can provide the fluid for such a cleaning operation, as further described below.

Examples of endoscope cleaning systems are described in U.S. Patent Publication No. 2019/0125176, filed Oct. 18, 2018, and titled, “Trocars,” U.S. Patent Publication No. 2021/0127963, filed Nov. 21, 2019, and titled “Intraoperative Endoscope Cleaning System,” and U.S. Patent Publication No. 2021/0127964, filed Nov. 21, 2019, and titled “Intraoperative Endoscope Cleaning System,” the disclosure of each of which is hereby incorporated by reference in its entirety.

FIG. 1 is a block diagram of a system 100 including a fluid delivery system 110 fluidically coupled to a surgical instrument 130, according to embodiments. The fluid delivery system 110 can optionally include an onboard power source 112. Alternatively, or additionally, the fluid delivery system 110 can optionally be coupled to an external power source 150. The fluid delivery system 110 includes a pump mechanism 116 and a controller 120. The fluid delivery system 110 can optionally include a liquid reservoir 114. Alternatively, or additionally, the fluid delivery system 110 can optionally be fluidly coupled to an external liquid source 170. An external gas source 160 can optionally be fluidly coupled to the fluid delivery system 110. Lines depicted in FIG. 1 connecting units can represent electrical, physical, and/or fluidic couplings.

The onboard power source 112 is an optional component integrated into the fluid delivery system 110. The onboard power source 112 powers the pump mechanism 116 and/or the controller 120. In some embodiments, the onboard power source can include a battery (e.g., a rechargeable battery). In some embodiments, the onboard power source 112 can include a fuel cell. In some embodiments, the onboard power source can be integrated into the same structure as the liquid reservoir 114, the pump mechanism 116, and/or the controller 120. For example, the onboard power source 112, the liquid reservoir 114, and the pump mechanism 116 can be disposed together in a housing (or one or more housing sections that couple together to form a housing). In some embodiments, the internal power supply can be configured as a backup power supply for cases when the external power source 150 is not available (e.g., when the external power supply is temporarily interrupted).

Optionally, an external power source 150 can be coupled to the fluid delivery system 110 to deliver power to one or more components of the fluid delivery system 110. In some embodiments, the external power source 150 can include a wall outlet. In some embodiments, the external power source 150 can include a battery or a battery pack physically separated from the fluid delivery system 110. In some embodiments, the external power source 150 can power the pump mechanism 116, the controller 120, and/or the onboard power source 112.

The liquid reservoir 114 is an optional component integrated into the fluid delivery system 110. The liquid reservoir 114 is configured to contain a liquid (e.g., wash liquid or solution), e.g., for cleaning a surgical instrument. In some embodiments, the washing fluid can include a saline solution, a buffered solution, a bio-compatible surfactant, and/or any other suitable wash solution, including those described in U.S. Patent Publication No. 2021/0127963. In embodiments where the fluid delivery system 110 is being used with a cleaning system, e.g., for cleaning an endoscope positioned within a trocar, the liquid reservoir 114 can be configured to contain a volume of liquid that is sufficient for conducting at least a predefined number of cleaning or wash cycles, e.g., between about 10 to about 2000 wash cycles, including sub-ranges and values therebetween. For example, the liquid reservoir 114 can be filled with enough liquid for cleaning a surgical instrument throughout the duration of a surgical procedure. In some embodiments, the liquid reservoir 114 can be pre-filled with different volumes of liquid, e.g., depending on the estimated number of times that a surgical instrument positioned within a body lumen or cavity may need to be cleaned. Therefore, for longer procedures that may require a greater number of wash sequences, the liquid reservoir 114 may be filled with a greater volume of liquid. In some embodiments, the liquid reservoir 114 can have a volume of at least about 5 mL, at least about 10 mL, at least about 15 mL, at least about 20 mL, at least about 25 mL, at least about 30 mL, at least about 35 mL, at least about 40 mL, at least about 45 mL, at least about 50 mL, at least about 55 mL, at least about 60 mL, at least about 65 mL, at least about 70 mL, at least about 75 mL, at least about 80 mL, at least about 85 mL, at least about 90 mL, or at least about 95 mL. In some embodiments, the liquid reservoir 114 can have a volume of no more than about 100 mL, no more than about 95 mL, no more than about 90 mL, no more than about 85 mL, no more than about 80 mL, no more than about 75 mL, no more than about 70 mL, no more than about 65 mL, no more than about 60 mL, no more than about 55 mL, no more than about 50 mL, no more than about 45 mL, no more than about 40 mL, no more than about 35 mL, no more than about 30 mL, no more than about 25 mL, no more than about 20 mL, no more than about 15 mL, or no more than about 10 mL. Combinations of the above-referenced volumes of the liquid reservoir 114 are also possible (e.g., at least about 5 mL and no more than about 100 mL or at least about 20 mL and no more than about 40 mL), inclusive of all values and ranges therebetween. In some embodiments, the liquid reservoir 114 can have a volume of about 5 mL, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 80 mL, about 85 mL, about 90 mL, about 95 mL, or about 100 mL.

Alternatively or additionally, an external liquid source 170 can be used to supply liquid to the fluid delivery system 110. The liquid source 170 may supply a liquid including, for example, a therapeutic agent, a drug, a saline solution, a wash solution, water, a biological fluid, and the like. The external liquid source 170 may be separate from the fluid delivery system 110 but be coupled to the fluid delivery system 110, e.g., via a fluid line. In some embodiments, the external liquid source 170 can be a fluid bag or other type of fluid containing element. In some embodiments, the external liquid source 170 can be a water line or other fluid line within a building that can be coupled via a faucet or other connection to the fluid delivery system 110. In some embodiments, both the external liquid source 170 and the liquid reservoir 114 may be present. The external liquid source 170 may be coupled to the liquid reservoir 114 and configured to fill the liquid reservoir 114 when needed (e.g., when a level of liquid within the liquid reservoir 114 is below a minimum level value). In some cases, the liquid from the external liquid source 170 (or from the liquid reservoir 114) may be processed by the fluid delivery system 110 prior to delivering the liquid to the surgical instrument 130 (or to the patient). For instance, such processing may include heating or cooling the liquid, filtering the liquid, pressurizing the liquid, and the like.

The fluid delivery system 110 may optionally be coupled to an external gas source 160. In some cases, the gas source 160 may be a source of air, $CO_2$, nitrogen, argon, or other inert gases, e.g., for propelling the delivering of a liquid into a surgical instrument 130. Such can be used to propel the liquid at high pressures for cleaning the surgical instrument or some other instrument disposed near or within the surgical instrument (e.g., an endoscope disposed within a trocar). Alternatively, the gas source 160 may provide a therapeutic agent, including, for example, a drug. In some cases, the gas may be processed within the fluid delivery system 110 prior to delivering the gas to the surgical instrument 130 (or to the patient). For instance, such processing may include heating or cooling the gas, filtering the gas, pressurizing the gas, and the like.

In some cases, more than one type of gas and/or liquid may be delivered by the fluid delivery system 110. For instance, the fluid delivery system 110 may be calibrated to deliver a first type of gas and/or a first type of liquid and may be recalibrated or adjusted (as further described below) to deliver a second type of gas and/or a second type of liquid. During a medical procedure, a first type of fluid such as a gas and/or liquid may be first received by the fluid delivery system 110 and delivered to the surgical instrument 130 (or to any other suitable instrument or the patient), and then a second type of fluid that is different from the first type of fluid may be received by the fluid delivery system 110 and delivered to the surgical instrument 130 (or to any other instrument or the patient). Additionally, or alternatively, more than one type of fluid may be supplied by the fluid delivery system 110 at one time. In some cases, when multiple gases and/or multiple liquids are present, the fluid delivery system 110 may be configured to mix or combine multiple gases and/or liquids.

The fluid delivery system 110 can optionally include an input/output (I/O) device 118, e.g., for communicating information to a user and/or receiving inputs from the user. The I/O device 118 can include any suitable input device or output device, such as a screen or display, a touch screen, a keyboard, a button, a switch, one or more signaling lights, a transmitter and/or receiver for transmitting signals to and/or receiving signals from an external device, a microphone, a speaker, and the like. In some embodiments, the user may input configuration or operation parameters for the fluid delivery system 110 via the I/O device 118. In some embodiments, the fluid delivery system 110 may be configured to transmit data an external device such as, for example, a smartphone, a mobile device, a computer, etc.

Additionally, or alternatively, I/O device 118 may be used to receive inputs from or send outputs to surgical instrument 130 (or any other instrument coupled to the fluid delivery system 110). For example, a control system associated with the surgical instrument 130 may determine how much fluid is needed to be transmitted to the surgical instrument 130, how quickly the fluid needs to be transmitted, pressure of the fluid that needs to be transmitted, or any other characteristics associated with the transmission of the fluid to the surgical instrument 130. Such flow characteristics data can be transmitted to the I/O device 118 (e.g., via a wired or a wireless transmission channel between the control system of the surgical instrument 130 and the I/O device 118) and processed by a controller 120 of the fluid delivery system 110.

In an example implementation, the fluid delivery system 110 is configured to deliver liquid (e.g., saline solution, water, and the like) and gas to the surgical instrument 130. In some embodiments, the gas can be used to drive or propel the delivery of the liquid. For instance, the gas source 160 may be used to pressurize the liquid and deliver the liquid to the surgical instrument 130, e.g., for a wash operation. In some embodiments, the gas source 160 can deliver gas at a pressure of between about 20 psi and about 50 psi, including all values and sub-ranges therebetween.

The pump mechanism 116 aids in delivering liquid to the surgical instrument 130. The pump mechanism 116 can include or form part of a centrifugal pump, peristaltic pump, lobe pump, rotary gear pump, horizontal split case pump, air operated pump, diaphragm pump, magnetically driven pump, a mechanically driven pump, an electrically driven pump, or any other suitable pump apparatus or combinations thereof. In a specific embodiment, the pump mechanism 116 can include a plunger, platform, shaft, or other suitable component that can be actuated (e.g., via a pump actuator) to compress a fluid line to deliver a liquid. For example, the pump mechanism 116 that includes a plunger can be actuated to compress a flexible housing or tubing that contains a liquid. The compression of the flexible housing or tubing can cause the liquid within the flexible housing or tubing to be driven toward the surgical instrument 130, e.g., to fill the lines for a wash or cleaning sequence.

The controller 120 is configured to control various components of the fluid delivery system 110, including, for example, the pump mechanism 116. In some embodiments, the controller 120 can be in communication with or include a processor and/or a user interface. Operation of the pump mechanism 116 can be automatic or user-controlled. In some embodiments, the user via the user interface can set parameters for when to activate the pump mechanism 116, e.g., to supply additional liquid for cleaning an endoscope. For example, the controller 120 can activate the pump mechanism 116 after each wash operation to fill the liquid lines for a subsequent wash operation. Alternatively, the controller 120 can activate the pump mechanism 116 to fill the liquid lines in response to an indication that an endoscope has been positioned for cleaning (e.g., based on signals received by the controller 120 from one or more sensors). In some embodiments, the controller 120 can activate the pump mechanism 116 to fill the liquid lines in response to a detection of a drop in pressure or volume in the liquid lines (e.g., based on signals received by the controller 120 from one or more sensors).

In some embodiments, the controller 120 via the I/O device 118 can be configured to display various data related to operations of the fluid delivery system 110. For instance, the controller 120 may display the volume of liquid dispensed, the volume of liquid remaining in the liquid reservoir 114, the volume flow rate of the liquid, the volume flow rate of the gas, and the like. In various embodiments, the data related to operations of the fluid delivery system 110 may be displayed on a screen associated with I/O device 118 or on a screen of an external device coupled to the fluid delivery system 110.

The surgical instrument 130 can be an instrument that is positioned within a patient. In some embodiments, the surgical instrument 130 can be a trocar that is placed within a patient to provide access into a body lumen or cavity of the patient. The body lumen or cavity can include the abdomen, thoracic cavity, a gallbladder, a bladder, a kidney, a lung, or any other body lumen or cavity. The trocar can be configured to receive one or more instruments, including, for example, imaging devices such as endoscopes. In use, the fluid delivery system 110 with the trocar can be used to clean such instruments.

In some embodiments, the fluid delivery system 110 can be configured to deliver predetermined, fixed volumes of liquid on an intermittent basis. Alternatively or additionally, the fluid delivery system 110 can be configured for continuous operation, e.g., by delivering multiple volumes or boluses of liquid on a periodic basis. For example, fluid delivery systems as described herein can operate (e.g., pump fluid) at predetermined frequencies. In some embodiments, the fluid delivery system can operate at frequencies of up to about 10 Hz.

While fluid delivery system 110 is described as delivering fluids to a surgical instrument (e.g., surgical instrument 130), it can be appreciated that the fluid delivery system 110 can be used to deliver controlled amounts of fluid to other types of devices, including, for example, tubing lines, IV lines, infusion systems, drug delivery system, microfluidics, etc.

Figure 2:
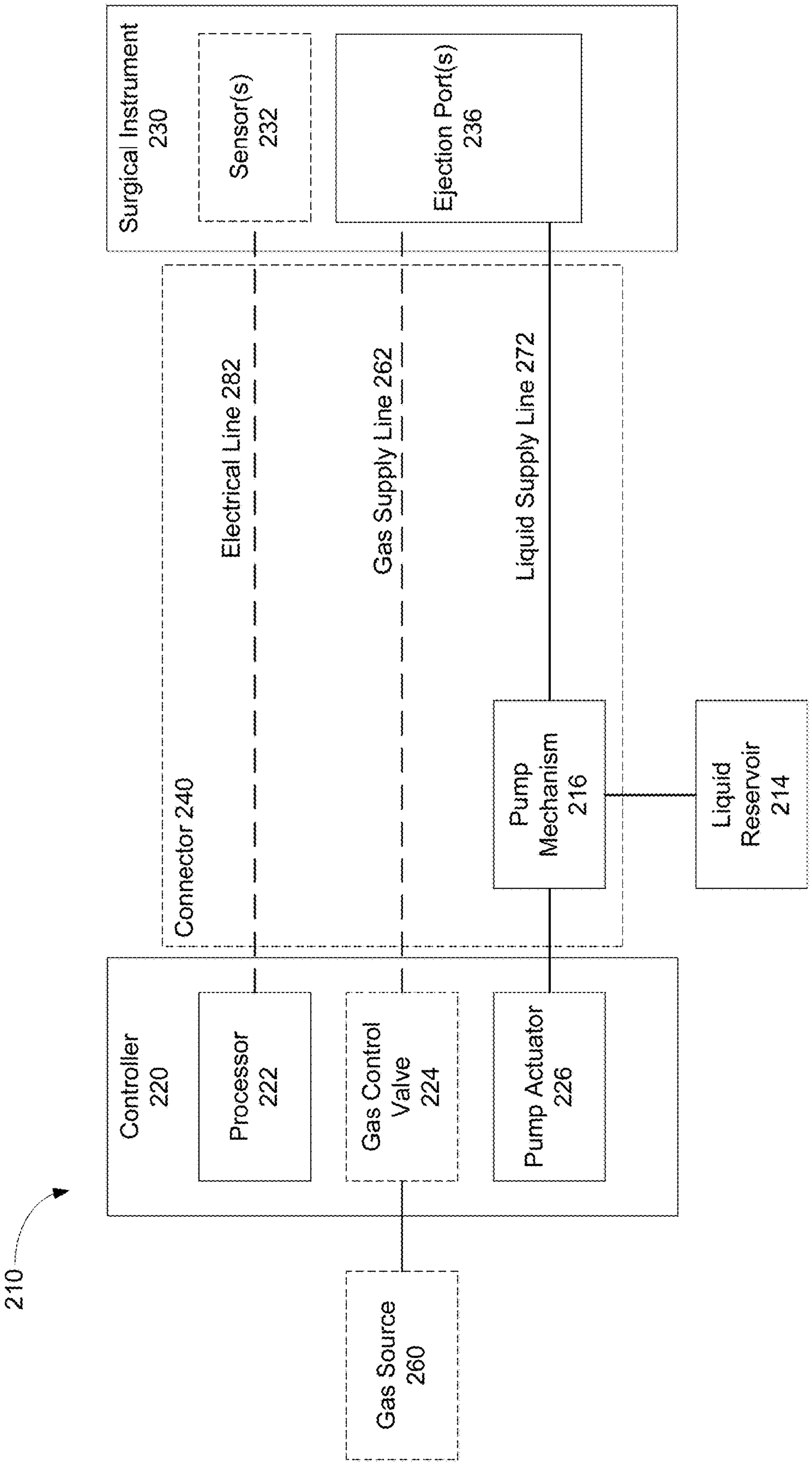
FIG. 2 is a block diagram of a fluid delivery system, according to an embodiment.

FIG. 2 provides a more detailed view of the liquid and gas connections of system 200 for delivering fluid to a surgical instrument 230. The system 200 can be structurally and/or functionally similar to other systems described herein, including, for example, system 100. For instance, the system 200 includes a fluid delivery system 210 which may be structurally and/or functionally similar to the fluid delivery system 110. As shown, the fluid delivery system 210 includes a controller 220. The fluid delivery system 210 is fluidically coupled to a surgical instrument 230 and an optional gas source 260. The controller 220 includes a processor 222, an optional gas control valve 224, and a pump actuator 226. The connector 240 can include an optional gas supply line 262, a liquid supply line 272, and an electrical line 282.

A liquid reservoir 214 can be fluidically coupled to a liquid supply line 272, with a pump mechanism 216 disposed along the coupling or line to control delivery of the liquid. Optionally, a gas source 260 can be fluidically coupled to a gas supply line 262, with a gas control valve 224 disposed along the coupling or line to control delivery of the gas. The processor 222 can be coupled to an electrical line 282, e.g., for sending and/or receiving data from electrical elements (e.g., sensor(s) 232) disposed within a surgical instrument 230.

In some embodiments, the liquid reservoir 214, the pump mechanism 216, the controller 220, and the gas source 260 can be the same or substantially similar to the liquid reservoir 114, the pump mechanism 116, the controller 120, and the gas source 160, as described above with reference to FIG. 1. Thus, certain aspects of the liquid reservoir 214, the pump mechanism 216, the controller 220, and the gas source 260 are not described in greater detail herein.

Optionally, the gas supply line 262, the liquid supply line 272, and the electrical line 282 can be contained within a connector 240. The connector 240 can be a cable that houses each of the lines. In some embodiments, the fluid delivery system 210 can include two parts that can be coupled to or decoupled from each other. The first part can include a controller 220 and a second part can include the connector 240. In one embodiment the connector 240 may have a first end that includes a connecting element configured to couple to the controller 220 (e.g., via a suitable first coupling connection between the controller 220 and the connector 240) and a second end that includes a connecting element configured to couple to the surgical instrument 230 (e.g., via a suitable second coupling connection between the connector 240 and the surgical instrument 230). Further details of the coupling between the connector 240 and the controller 220 are described with reference to later figures.

The processor 222 can be coupled to an electrical line 282, e.g., for sending and/or receiving data from electrical elements disposed in the surgical instrument. For example, the processor 222 via the electrical line 282 can be configured to receive data from the one or more sensors 232 of the surgical instrument 230. The one or more sensors 232 can provide information to the processor 222 for controlling the delivery of liquid and/or gas. For example, when used for cleaning an endoscope disposed in a trocar, the one or more sensors 232 may be disposed along the trocar, e.g., to detect when an endoscope is being retracted within the trocar for initiating a wash operation. In some embodiments, the electrical line 282 can include conductive wiring. In some embodiments, the conductive wiring can be composed of copper, silver, brass, gold, titanium, stainless steel, carbon steel, or any combination thereof. In some embodiments, the electrical line 282 can be housed within the connector 240 and insulated from external elements. When the electrical line 282 is integrated into or housed in a connector 240, the first coupling connection between the controller 220 and the connector 240 can include a first electrical connection connecting the electrical line 282 with various electrical components of the controller 220, and the second coupling connection between the connector 240 and the surgical instrument 230 can include a second electrical connection connecting the electrical line 282 with various electrical components of the surgical instrument 230.

While sensors are provided as an example of an electrical component, it can be appreciated that the processor 222 can be coupled to other types of electrical components, e.g., actuation elements, pumps, electrical valves, etc. In some cases, the electrical line 282 may have multiple data transmission lines for transferring various data in any suitable direction between electrical components of the controller 220 and electrical components of the surgical instrument 230. Further, in addition to transferring data, the electrical line 282 may be configured to transfer power. For example, the electrical line 282 may be configured to transfer power between the controller 220 and the surgical instrument 230.

In embodiments where there is gas delivery via the fluid delivery system 210, an optional gas source 260 and an optional gas control valve 224 can be fluidically coupled to the surgical instrument via the gas supply line 262. In some embodiments, the gas supply line 262 can be configured to supply gas to one or more ejection port(s) 236 of the surgical instrument 230. The gas can be used for various applications, including, for example, for drying components of the surgical instrument and/or other devices disposed therein, for propelling the delivery of a liquid, for inflating balloons or other flexible membranes, and the like. In some embodiments, the gas supply line 262 can include flexible tubing. In some embodiments, the tubing can be composed of a polymer, polyvinylchloride (PVC), polyurethane, Tygon®, acrylic, metal (e.g., copper or stainless steel), silicone, or any other suitable material. The controller 220 can be configured to control the operation of the gas control valve 224, e.g., to control the delivery of the gas. In some embodiments, the controller 220 can control the gas control valve 224 to close, open, or partially open, e.g., in response to signals received from sensor(s) 232.

The liquid supply line 272 includes tubing for supplying liquid to the surgical instrument 230. In some embodiments, one or more valves can be disposed within the liquid supply line 272, e.g., to control when liquid is being delivered and/or to control volume of liquid being delivered. In one implementation, the liquid supply line includes a flexible liquid channel having an inflow end and an outflow end. The inflow end of the flexible liquid channel is connected to the fluid reservoir 214 via a first channel having a first valve. The outflow end of the flexible liquid channel is connected to the surgical instrument 230 (and, in particular, one or more ejection port(s) 236) via a second channel having a second valve. In some embodiments, the flexible liquid channel can be composed of a polymer, PVC, polyurethane, Tygon®, acrylic, silicone, or any other suitable material.

The pump actuator 226 can actuate the pump mechanism 216 to deliver liquid to the surgical instrument 230 via the liquid supply line 272. The pump actuator 226 can include an electrical motor and/or other drive mechanisms for actuating the pump mechanism 216. In some embodiments, the pump actuator 226 can be powered by a battery, a wall outlet, or any other suitable power mechanism. The pump mechanism 216 can be a plunger, shaft, clamp, or other suitable structure that can be actuated to compress flexible tubing containing the liquid, e.g., to pump the liquid. In some embodiments, the pump mechanism 216 can be configured to compress a flexible liquid channel of the liquid supply line 272. In some embodiments, the pump mechanism 216 can define a space for receiving a flexible liquid channel and can include a base element configured to be adjacent to a first side of the flexible liquid channel and a compressing element (e.g., a plunger, a shaft, a clamp, a vise, etc.t) configured to be adjacent to a second side of the flexible liquid channel. In such embodiments, the pump mechanism 216 can be configured to squeeze or clamp down on the flexible liquid channel disposed between the compressing element and the base element. In some embodiments, the pump mechanism 216 can include a plunger with a base that can engage with and compress down on a flexible liquid channel. In some embodiments, the pump mechanism 216 can be disposed in the connector 240, such as, for example, a controller connection of the connector 240. In some embodiments, the pump mechanism 216 can be disposed within a housing of the controller 220. In such instances, the pump mechanism 216 can be configured to extend out of the housing, e.g., to compress on a flexible liquid channel. Further details of pump mechanisms 216 are described with reference to FIGS. 7A-10B.

As described above, in some embodiments, the liquid supply line 272 can include one or more valves, e.g., for controlling the delivery of liquid to the surgical instrument 230. The one or more valves can selectively open to allow for pumping or refilling of the liquid line. In use, the pump mechanism 216 can be configured to apply pressure to a section of the flexible liquid channel that is disposed between an upstream valve and a downstream valve (e.g., by pressing a portion of the flexible liquid channel against a surface or base). In response to the application of pressure, the flexible tube can compress and cause a downstream valve to open and the liquid to flow from the flexible liquid channel towards ejection port(s) 236. Further, upon removing the pressure from the flexible liquid channel, the flexible liquid channel can return to its original uncompressed state, and the downstream valve can close while the upstream valve opens, thereby allowing liquid from the liquid reservoir 214 to enter and refill the flexible liquid channel. The displacement of the pump mechanism 216, the configuration and placement of the pump mechanism 216 relative to the flexible liquid channel, and the design of the downstream and upstream valves can each contribute to the volume of liquid that is delivered in response to each application of pressure by the pump mechanism 216.

The downstream and upstream valves may be any suitable valves that are designed to open and close in the conditions as described above. For instance, the first and the second valves can be one-way check valves, such as, for example, ball check valves, diaphragm check valves, swing check valves, or any other suitable check valves. When the flexible liquid channel is compressed, the increase in pressure therein can result in the opening of the downstream valve. Next, when the flexible liquid channel returns to its uncompressed state, the decrease in pressure therein can result in the opening of the upstream valve.

In an example implementation, the processor 222 can receive information from the sensor(s) 232 and, based on that information, control the delivery of the gas and/or liquid, e.g., by controlling the gas control valve 224 and/or the pump actuator 226. For example, when the surgical instrument is a trocar, one or more sensors 232 disposed in the trocar can detect a position of the distal end of an endoscope positioned within the trocar. When the sensor(s) 232 detect that the endoscope is retracted and/or positioned for cleaning, the sensor(s) 232 can send that data to the processor 222, which can activate the gas control valve 224 to open, e.g., to deliver gas to propel the delivery of liquid into the trocar. Subsequently, the processor 222 can control the pump actuator 226 and/or pump mechanism 216 to pump additional liquid into the liquid supply line 272, e.g., to prime the system for subsequent cleaning cycles.

Figure 3:
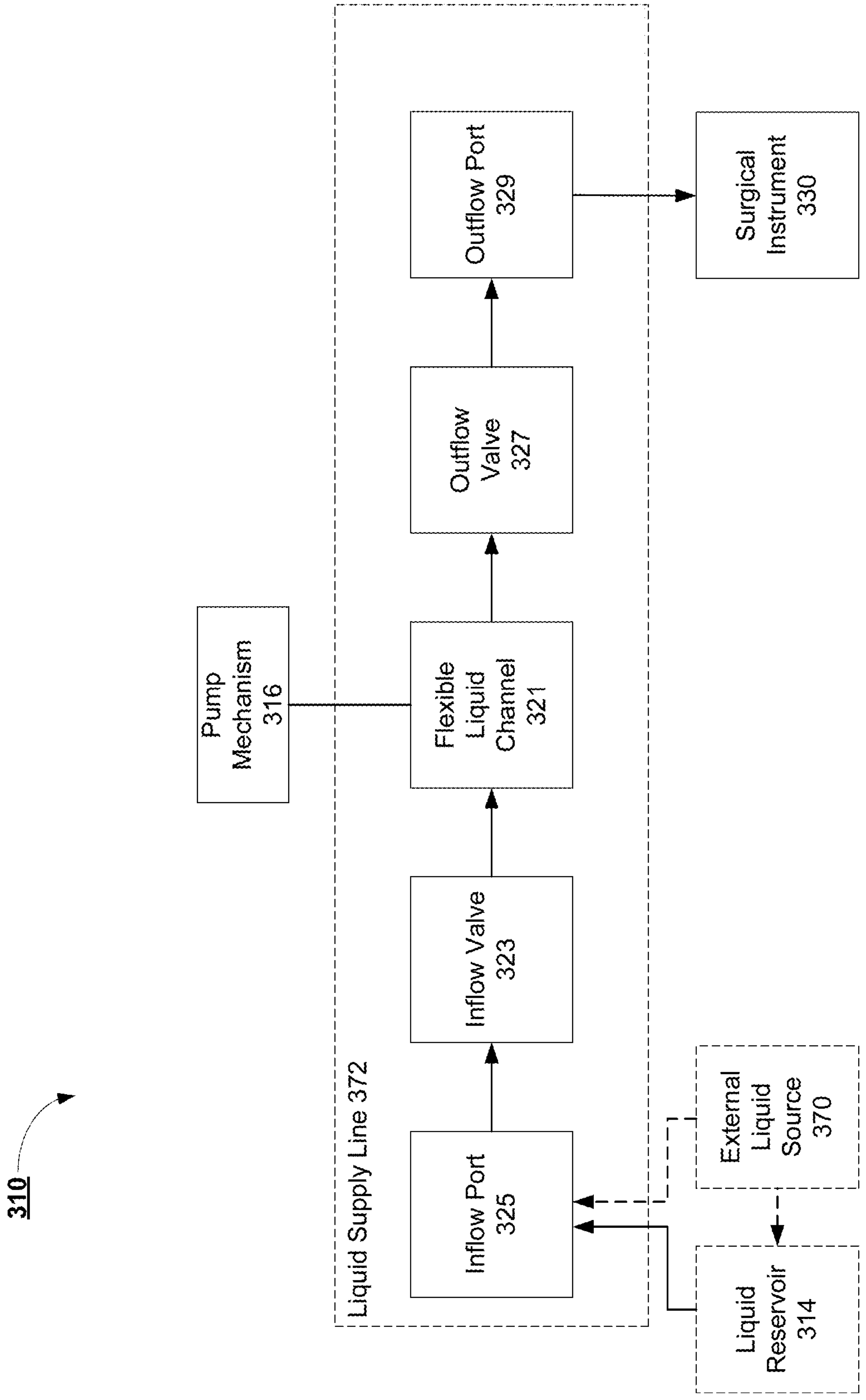
FIG. 3 is a block diagram of a liquid supply line, according to an embodiment.

FIG. 3 shows an embodiment of the fluid delivery system 310, which may be similar in form and/or in function to the fluid delivery system 110 or fluid delivery system 210. For instance, the fluid delivery system 310 includes a pump mechanism 316 that is configured to interact with a flexible liquid channel 321. In the example embodiment, the flexible liquid channel 321 can form a part of a liquid supply line 372, which may be similar in form and/or in function to the liquid supply line 272, as shown and described with reference to FIG. 2. The inflow port 325 can be fluidically connected to the liquid reservoir 314 and/or an external liquid source 370. The outflow port 329 can be fluidly connected to a surgical instrument 330 (e.g., a trocar).

The pump mechanism 316 can be configured to interact with a flexible liquid channel 321. In an embodiment, the flexible liquid channel 321 can be implemented as a flexible tubing. In some embodiments, the flexible tubing can have an inner diameter of between about 0.01 inches and about 0.1 inches, including all values and sub-ranges therebetween, for example, including about 0.06 inches. In some embodiments, the flexible tubing can have an outer diameter of between about 0.1 inches and about 0.5 inches, including all values and sub-ranges therebetween, including, for example, about 0.13 inches. In some embodiments, the flexible tubing can have a hardness of between about 10 and about 70 on the Shore A scale. The pump mechanism 316 can compress the flexible liquid channel 321, which can cause an increase in pressure that can open the outflow valve 327. A fixed volume of liquid can then pass through the outflow valve 327 and flow toward the outflow port 329. The pump mechanism 316 can then retract, allowing the flexible liquid channel 321 to return to its uncompressed state. When the flexible liquid channel 321 returns to its uncompressed state, the outflow valve 327 closes while the inflow valve 323 can open, e.g., due to a pressure difference between its inlet and outlet. Liquid from the liquid reservoir 314 can then pass via the inflow valve 323 into the flexible liquid channel 321, e.g., to fill the flexible liquid channel 321 with liquid again. While not depicted, the pump mechanism 316 can be actuated using a pump actuator (e.g., pump actuator 226), which can be controlled via a controller (e.g., controller 120, 220).

Similar to the fluid delivery system 210, at least a portion of the liquid supply line 372 can be part of a connector (e.g., connector 240). In some embodiments, the pump mechanism 316 can be implemented as a plunger, a clamp, or any other suitable structure capable of compressing a flexible liquid channel 321.

Figure 4A:
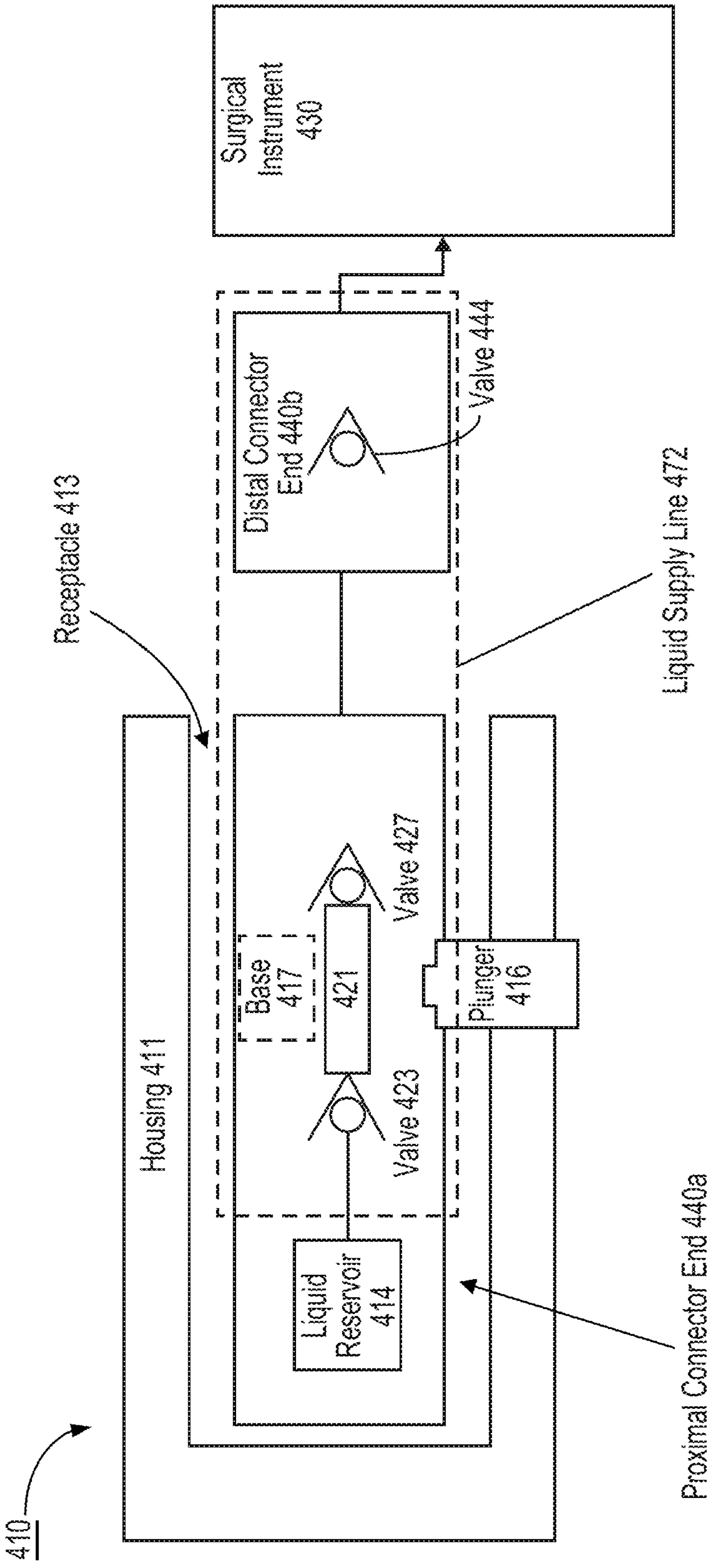
FIG. 4A is a diagram of a fluid delivery system including a housing that defines a receptacle for receiving a liquid supply line, according to an embodiment.

FIG. 4A shows an embodiment of a fluid delivery system 410, which may be similar in form or in function to any of the fluid delivery systems discussed herein. For example, the fluid delivery system 410 can include components that are structurally and/or functionally similar to other fluid delivery systems described herein, including, for example, fluid delivery systems 110, 210, 310.

The fluid delivery system 410 includes a housing 411 that can house or support one or more components that control the delivery of liquid and/or gas. For example, the housing 411 can house a pump mechanism implemented as a plunger 416 that can be actuated (e.g., depressed) to pump fluid disposed within a flexible fluid channel or flexible tubing 421. The housing 411 can define a receptacle 413, e.g., for receiving a proximal connector end 440*a* of the connector. The proximal connector end 440*a* can include a liquid reservoir 414, valves 423, 427, and the flexible tubing 421. As described above with reference to FIG. 3, the plunger 416 can be actuated to compress the flexible tubing 421 to cause downstream valve 427 to open and liquid to pump through the valve 427 toward a surgical instrument 430. The plunger 416 can then be released or retracted to allow the flexible tubing 421 to return to its uncompressed state. In response to the flexible tubing 421 returning to its uncompressed state, the valve 427 can close and the valve 423 can open to allow liquid from the liquid reservoir 414 to refill the flexible tubing 421. The liquid reservoir 414 can have a size and configuration that allows it to fit within a housing of the proximal connector end 440*a*. The liquid reservoir 414 can be pre-filled with a liquid, e.g., using an external liquid source such as a syringe.

The fluid delivery system 410 can be configured to deliver a fixed volume of liquid during each pump cycle, i.e., during each actuation of the plunger 416. The fixed volume of liquid can be a small volume a liquid, which the components of the fluid delivery system 410 as described herein are particularly designed to deliver. In some embodiments, the fixed volume of liquid can include at least about 1 μL, at least about 2 μL, at least about 3 μL, at least about 4 μL, at least about 5 μL, at least about 6 μL, at least about 7 μL, at least about 8 μL, at least about 9 μL, at least about 10 μL, at least about 11 μL, at least about 12 μL, at least about 13 μL, at least about 14 μL, at least about 15 μL, at least about 16 μL, at least about 17 μL, at least about 18 μL, or at least about 19 μL of liquid. In some embodiments, each fixed volume of liquid can include no more than about 20 μL, no more than about 19 μL, no more than about 18 μL, no more than about 17 μL, no more than about 16 μL, no more than about 15 μL, no more than about 14 μL, no more than about 13 μL, no more than about 12 μL, no more than about 11 μL, no more than about 10 μL, no more than about 9 μL, no more than about 8 μL, no more than about 7 μL, no more than about 6 μL, no more than about 5 μL, no more than about 4 μL, no more than about 3 μL, or no more than about 2 μL. Combinations of the above-referenced volumes for each fixed volume of liquid are also possible (e.g., at least about 1 μL and no more than about 20 μL or at least about 5 μL and no more than about 15 μL), inclusive of all values and ranges therebetween. In some embodiments, each fixed volume of liquid can include about 1 μL, about 2 μL, about 3 μL, about 4 μL, about 5 μL, about 6 μL, about 7 μL, about 8 μL, about 9 μL, about 10 μL, about 11 μL, about 12 μL, about 13 μL, about 14 μL, about 15 μL, about 16 μL, about 17 μL, about 18 μL, about 19 μL, or about 20 μL of liquid.

In some embodiments, the proximal end connector 440*a* can optionally include a base 417. The base 417 can be a platform or protrusion (e.g., a cylindrical shim) that pushes the flexible tubing 421 toward the plunger 416, e.g., for greater engagement or compression of the flexible tubing 421. The base 417 can be configured to provide for more controlled compression of the flexible tubing 421, which can enable more controlled and precise delivery of liquid during each pump cycle.

The connector can further include a distal end connector 440*b*. The distal end connector 440*b* can include a valve 444, e.g., for preventing leaking or movement of liquid due to hydrostatic pressures. Similar to the valves 423, 427, the valve 444 can be configured to transition between open and closed states in response to a pressure difference between the inlet and outlet of the valve. The valves 423, 427, 444 can operate to prevent movement of liquid when the plunger 416 is not being actuated to pump the liquid. For example, each of the valves 423, 427, 444 can be selected to be one-way check valves that open under specific cracking pressures.

Figure 4B:
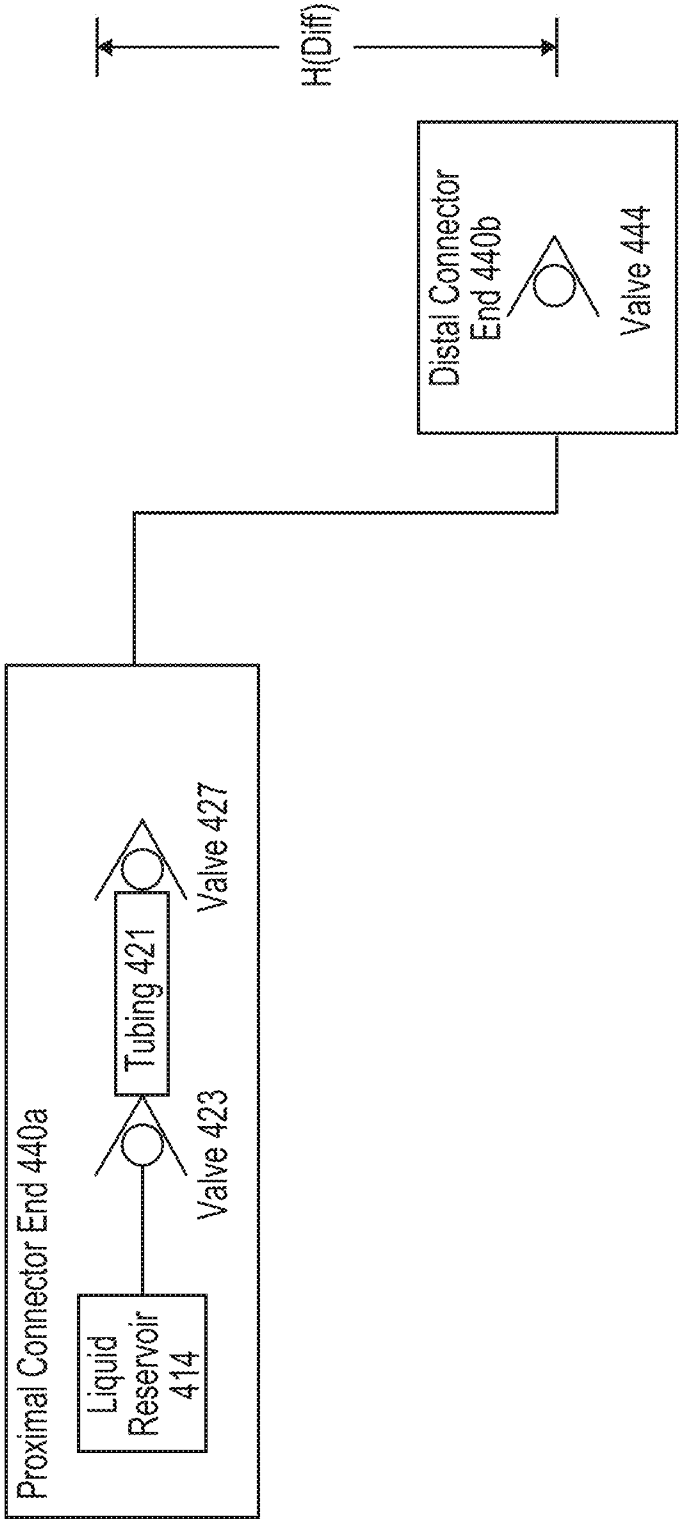
FIG. 4B is a diagram of a fluid delivery system showing differences in height between the proximal and distal ends of a liquid supply line, according to an embodiment.

In use, the proximal connector end 440*a* and the distal connector end 440*b* may be at different heights, e.g., due to their coupling to different components of a larger system. For example, the proximal connector end 440*a* may be coupled to a controller of a fluid delivery system, while the distal connector end 440*b* may be coupled to a surgical instrument (e.g., a trocar) that has been placed within a patient. Depending on the relative location of the controller and the surgical instrument, a difference of H(Diff) may exist between the height of the proximal connector end 440*a* and the distal connector end 440*b*. FIG. 4B depicts such a scenario, where the proximal connector end 440*a* and the distal connector end 440*b* are set a different heights.

With a height differential H(Diff) between the proximal connector end 440*a* and the distal connector end 440*b*, liquid that is within the connector may generate hydrostatic pressure, e.g., due to gravity, which can cause leaking of the liquid out of the distal end connector 440*b*. This problem is exacerbated when the H(Diff) is particularly large. With such large differences in height, the hydrostatic pressure from the water column due to gravity would cause liquid to leak if it is able to overcome the cracking pressure of the three valves 423, 427, 444. This can be represented by the Bernoulli Principle, as shown in the following equation:

$$P_1 + \frac{1}{2}\rho v_1^2 + \rho g h_1 = P_2 + \frac{1}{2}\rho v_2^2 + \rho g h_2$$

where $P_1$ is the pressure at a first elevation or height, $P_2$ is the pressure at a first elevation or height, ρ is fluid density, g is acceleration due to gravity, $v_1$ is velocity at the first elevation, $v_2$ is velocity at the second elevation, $h_1$ is the height at the first elevation, and $h_2$ is the height at the second elevation.

To mitigate against passive flow, valves with cracking pressure that can overcome the hydrostatic pressures of the liquid column were selected. Design considerations in the plunger 416, the base 417, and the flexible tubing 421 were also adjusted such that the compression of the flexible tubing 421 by the plunger 416 can cause sufficient increase in pressure to open the valves and pump liquid toward the surgical instrument 430. For example, the addition of the base 417 (e.g., a cylindrical shim) can be used to close the gap or distance between the plunger 416 and the flexible tubing 421, thereby enabling full or a greater degree of compression of the flexible tubing 421. The greater compression can cause a greater increase in pressure, which can open the downstream valve 427 for allowing liquid to flow toward the surgical instrument 430. Alternatively or additionally, the profile of the plunger 416 can be adapted to be smaller, allowing for a greater compressive force to be concentrated on a smaller area of the flexible tubing 421, thus increasing the pressure against the flexible tubing 421. The fluid delivery system 410 was also adapted, e.g., via adapting the controller, to have the plunger 416 always be engaged when the flexible tubing 421 is inserted into the receptacle 413. Such modifications and/or additions prevented passive flow of the liquid with height differentials of up to at least about 3 feet.

The base 417 and the profile of the plunger 416 also aided in increasing the consistency of fluid delivery. For example, when the flexible tubing 421 is not sufficiently compressed, fluid ejection volumes may be highly variable and result in instances where no liquid is delivered during a pump cycle. With the addition of the base 417 (e.g., a cylindrical shim), compression of the flexible tube 421 was more consistent. The plunger profile, by being smaller (e.g., being reduced from a larger width to a smaller width), also contributed to more consistent fluid delivery.

Figure 6A:
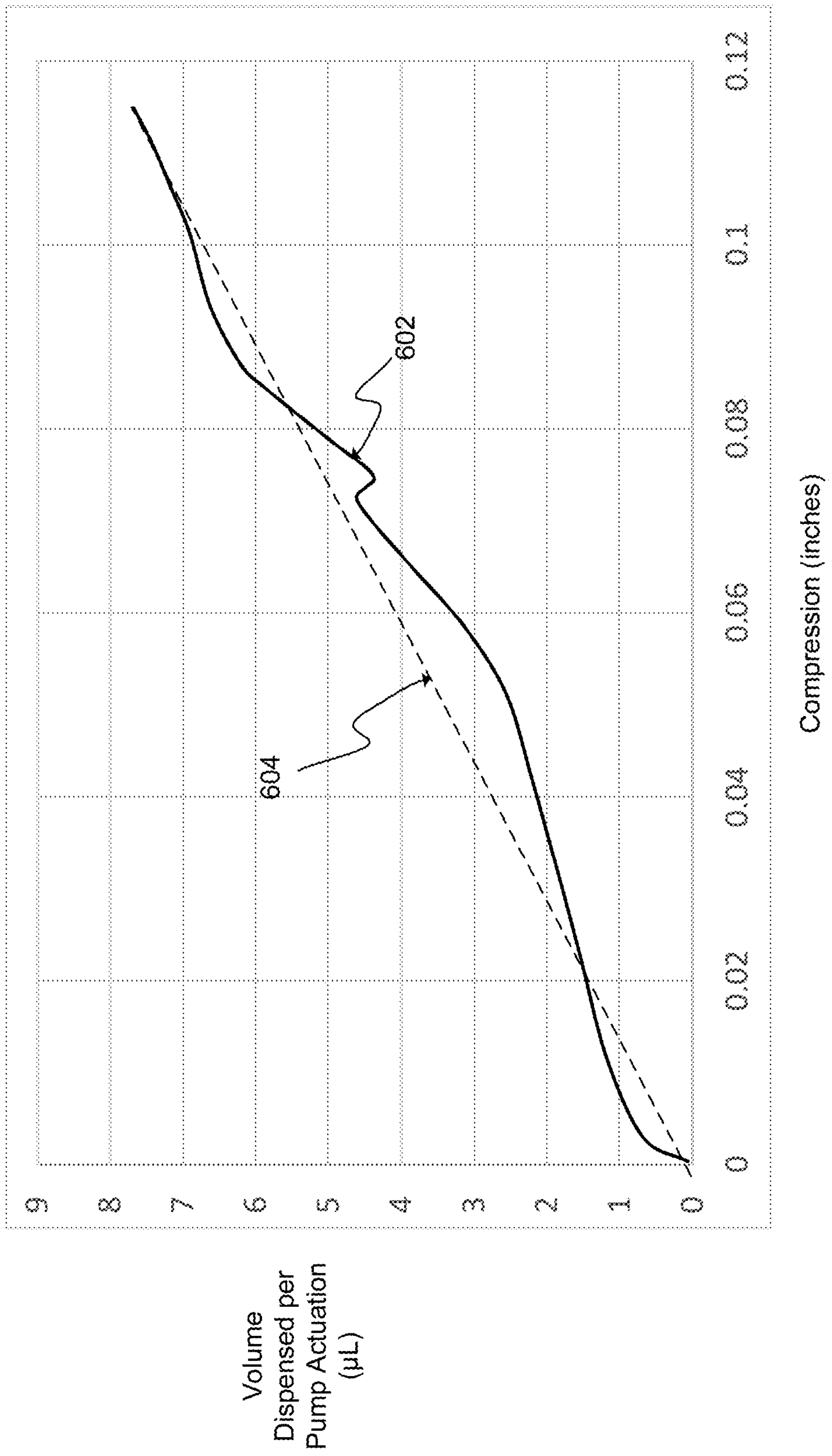
FIG. 6A variation in dispensed volume of a fluid delivery system as a function of compression of a fluid delivery line, according to embodiments.
Figure 6B:
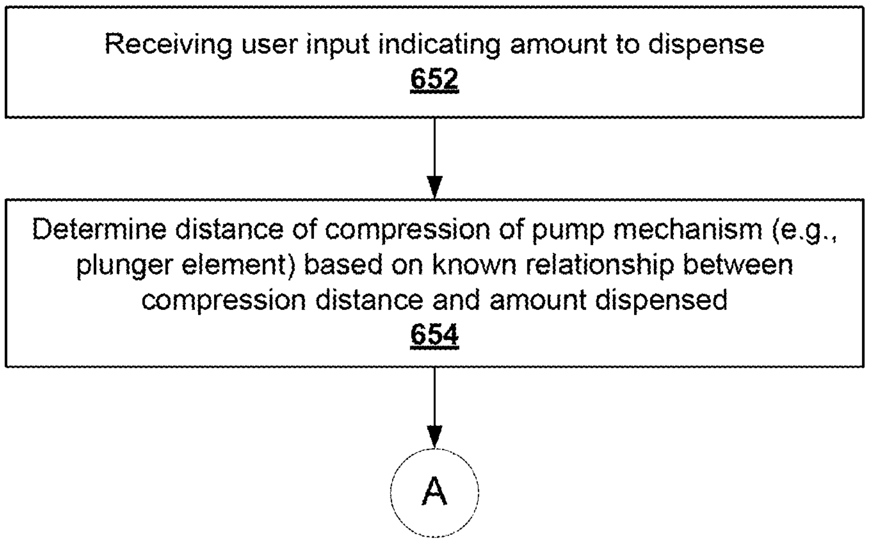
FIG. 6B is a flow diagram of the operation of a fluid delivery system for dispensing a predetermined volume of liquid, according to an embodiment.
Figure 7A:
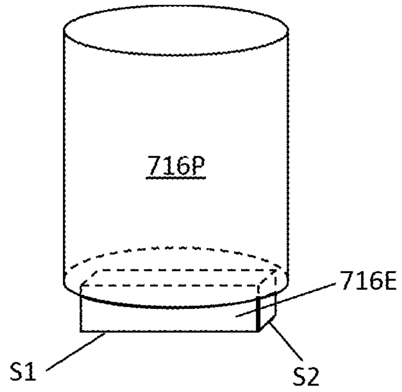
FIGS. 7A and 7B depict different views of an example pump mechanism, according to embodiments.
Figure 8A:
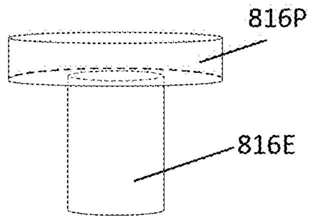
FIGS. 8A and 8B depict different views of an example pump mechanism, according to embodiments.
Figure 10A:
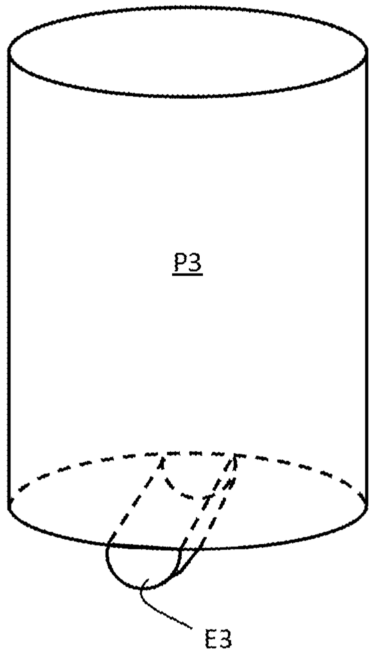
FIGS. 10A and 10B depict additional variations of pump mechanisms, according to embodiments.
Figure 10B:
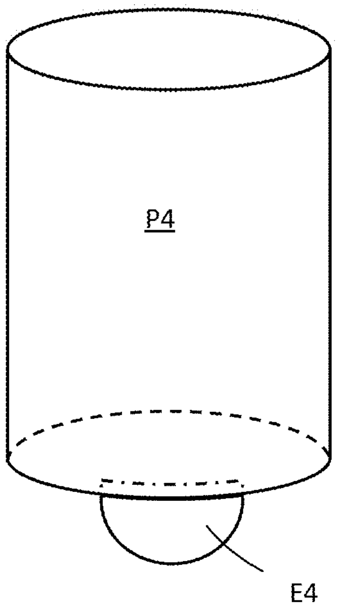
Figure 21A:
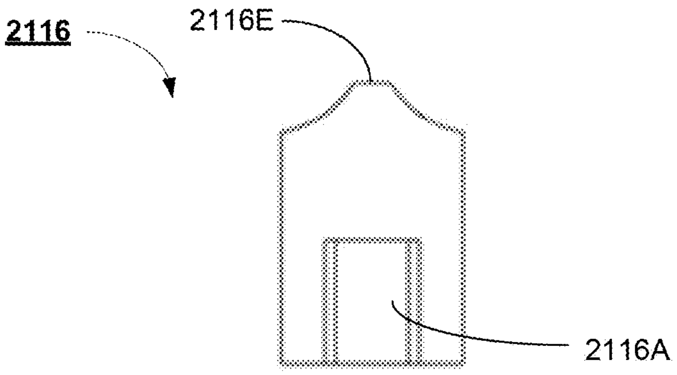
FIGS. 21A-21C depict different views of an example pump mechanism, according to embodiments.
Figure 21B:
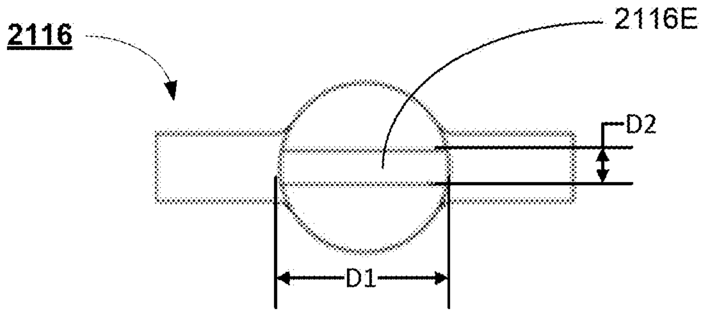
Figure 21C:
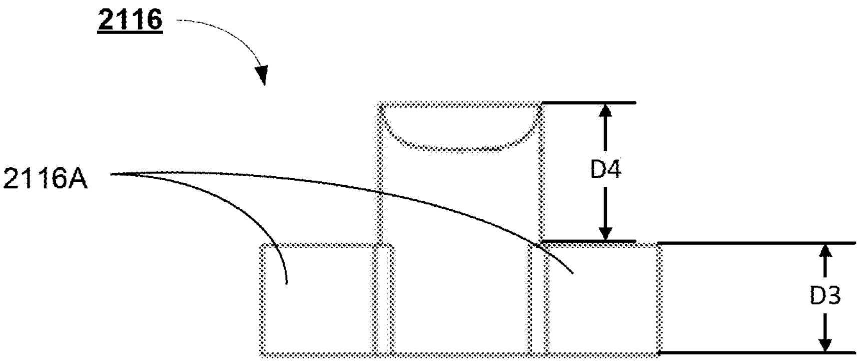

FIGS. 7A-10B and 21A-21C depict different variations of plunger profiles, according to embodiments. As depicted in FIGS. 9A and 9B, the plunger profile can be decreased from D1 to D2, e.g., to allow for a greater compressive force to be concentrated on a smaller area of flexible tubing (e.g., flexible tubing 421). FIGS. 7A and 7B depict a plunger 716P including a slotted design. In particular, the plunger 716P can have a rectangular protrusion 716E with sides S1, S2. In some embodiments, side S1 can be between about 0.1 inches and 0.5 inches, including about 0.25 inches and other values and ranges therebetween. In some embodiments, side S2 can be between about 0.01 inches and about 0.1 inches, including about 0.05 inches and other values and ranges therebetween. In use, the design of the plunger 716P has been found to be effective at delivering liquid volumes of less than about 5 μL. For example, with full compression of a flexible tubing 421 that is formed of silicone with a Shore A hardness of about 50 and having an inner diameter of 1⁄16" (about 0.06 inches) and an outer diameter of 1⁄8" (about 0.13 inches), the slotted plunger design as depicted in FIGS. 7A and 7B provided consistent delivery of a fixed volume of fluid between about 2 μL and about 3 μL. With different degrees of compression (e.g., different displacement of the plunger relative to the flexible tubing), different fixed volumes of liquid can also be achieved, as further described below with reference to FIGS. 6A-6B. FIGS. 8A and 7B depict another example of a plunger 816P, having a cylindrical protrusion 816E. Similar to the plunger 716P depicted in FIGS. 7A and 7B, the plunger 816P has a smaller region that is configured to contact the flexible tubing (e.g., flexible tubing 421) and therefore can concentrate the compression over a smaller area. FIGS. 10A-10B depict additional examples of plunger profiles, including a plunger P3 a rounded or circular slot E3 (see FIG. 10A) and a plunger P4 with a rounded or spherical bump E4 (see FIG. 10B). Each of these plunger profiles can accomplish different liquid delivery behavior, and different designs can be better suited for delivering different fixed volumes of liquid and/or for interaction with different flexible tubing and/or bases (e.g., shims). FIGS. 21A-21C depict another example of a pump mechanism implemented as a plunger 2116 including protrusion or end 2116E that can be configured to contact and compress a flexible tubing. The portion of the end 2116E that is configured to contact the flexible tubing can have a substantially rectangular shape. In particular, the bottom of the end 2116E, as depicted in FIG. 21B, can have a slot that has a maximum length D1 and a maximum width D2. In some embodiments, D1 can be between about 0.1 inches and 0.5 inches, including about 0.25 inches and other values and ranges therebetween. In some embodiments, D2 can be between about 0.01 inches and about 0.1 inches, including about 0.05 inches and other values and ranges therebetween. The sides of the slot can be curved or rounded, e.g., as shown in FIGS. 21A and 21B. The plunger 2116 can also include elements 2116A implemented as tabs or wings that allow the plunger 2116 to be coupled to a pump actuator (e.g., a solenoid valve, pump, etc.), as shown in the side views of FIGS. 21A and 21C. For example, the elements 2116A can have sufficient height D3 to allow for such coupling to an actuator. The elements 2116A can also be positioned a distance D4 back from the bottom of the slot so that the elements 2116A do not interfere with the operation of the slot in compressing the flexible tubing. For example, the distance D4 enables the slot to make contact with and fully compress the flexible tubing before the elements 2116A would contact the connector housing or receptacle supporting the flexible tubing.

While liquid reservoirs 214, 314, 414 are described with reference to FIGS. 2-4B (and described in later embodiments herein), it can be appreciated that a reservoir can be designed as any structure and/or component that is capable of holding a volume of fluid. For example, in some implementations, a reservoir can be a lumen, channel, or tubing or other elongate structure that can contain or hold a volume of fluid. In some implementations, the reservoir can include coiled tubing. Such tubing can be contained within the housing 411 or some other type of housing associated with the fluid delivery systems described herein.

Figures 5A, 5B, 5C:
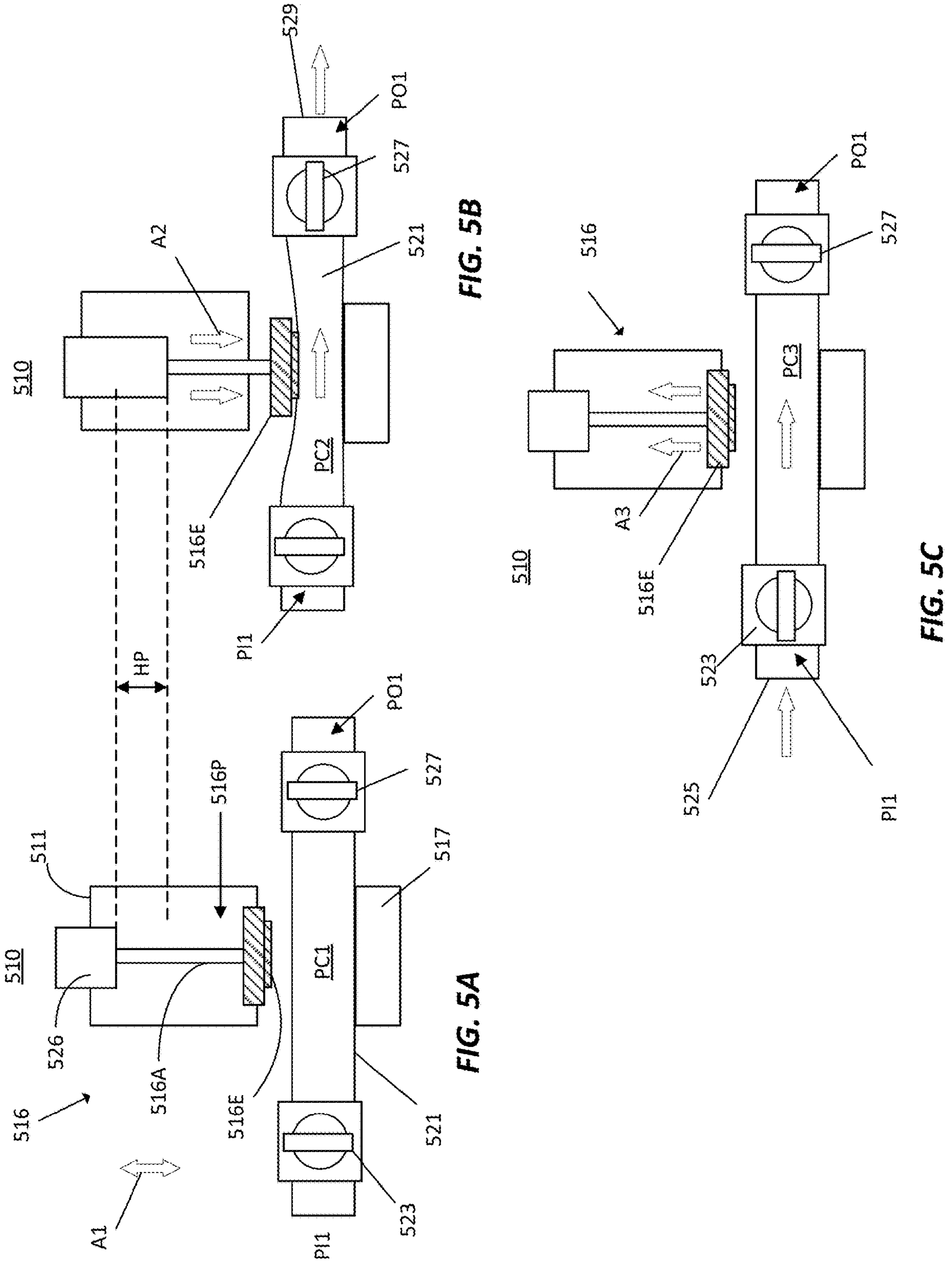
FIGS. 5A-5C show the operation of a pump mechanism of a fluid delivery system, according to an embodiment.

FIGS. 5A-5C provide a more detailed view of the pumping operation of a fluid delivery system, according to embodiments. The fluid delivery system 510 includes a pumping mechanism 516, flexible liquid channel 521, an inflow valve 523, and an outflow valve 527. In the example embodiments, the valves 523 and 527 can be one-way check valves. The fluid delivery system 510 may be similar in form or in function to any fluid delivery systems discussed herein, including, for example, fluid delivery systems 110, 210, 310, 410. For example, the flexible liquid channel 521 may be similar to the flexible liquid channels 321, 421, the pump mechanism 516 can be similar to the pump mechanisms 316, 416, etc.

As depicted in FIGS. 5A-5C, the pumping mechanism 516 includes a plunger 516P that can move relative to a housing 511, e.g., to compress the flexible liquid channel 521. The housing 511 can be a housing associated with a controller of the fluid delivery system 510 (e.g., controller 120, 220). The housing 511 can support the plunger 516P such that the plunger 516P can extend out of the housing 511 and contact the flexible liquid channel 521. In the example implementation, the plunger 516P includes an arm element 516A configured to move linearly as indicated by arrow A1 towards and/or away from the flexible liquid channel 521. The plunger 516P includes a plunger end 516E configured to contact and press onto a section of the flexible liquid channel 521.

The flexible liquid channel 521 can be disposed between the plunger 516P and a surface 517. In some embodiments, the surface 517 can include an optional cylindrical shim or other structure that pushes the flexible liquid channel 521 toward the plunger 516P, e.g., to increase the compression of the flexible liquid channel 521 and provide for more consistent fluid volume delivery. While the plunger 516P is shown above the flexible liquid channel 521 and the surface 517 as being below the liquid channel 521, in other implementations, the plunger 516P may be below the flexible liquid channel 521 and the surface 517 may be above the liquid channel 521. Further, any other configuration of the plunger 516P and the surface 517 may be used.

FIG. 5A shows the plunger 516P prior to being actuated to compress the flexible liquid channel 521. FIG. 5B shows the plunger 516P compressing the flexible liquid channel 521, thereby changing the shape of the flexible liquid channel 521 (e.g., the flexible liquid channel 521 is being squeezed between the plunger 516P and the surface 517). FIG. 5C shows the plunger 516P as it is being withdrawn away from the flexible liquid channel 521.

When the plunger 516P is not engaged with the flexible liquid channel 521, as shown in FIG. 5A, the difference between liquid pressure within the flexible liquid channel 521 (pressure PC1) and the pressure at the inflow (pressure PI1) is less than a cracking pressure of the check valve 523. Further, the difference between the pressure at the outflow (pressure PO1) and PC1 is less than the cracking pressure of the check valve 527. Thus, valves 523 and 527 are shown to be closed in FIG. 5A.

When the plunger 516P compresses the flexible liquid channel 521, as indicated by arrows A2 in FIG. 5B, this results in increased pressure PC2 within the liquid channel 521. The plunger 516B can be moved linearly by a distance HP to compress the flexible liquid channel 521. The distance HP can be adjusted, e.g., via inputs by a user into a controller (e.g., controller 120, 220) or manually, to control the degree of compression of the liquid channel 521. In various embodiments, the distance HP can be adjusted to deliver a specific volume of liquid. For example, the fluid delivery device 510 can be calibrated to determine the distance HP that the plunger 516P should be depressed to achieve different volumes of liquid delivery. In some cases, the fluid delivery system 510 may be calibrated based on a type of liquid used. For example, a first relation between volume delivered and HP may be determined for a first liquid and a second relation between volume delivered and HP may be determined for the second liquid. Further details of such a calibration process are described with reference to FIGS. 6A-6B.

In some embodiments, the distance HP can be adjusted to deliver different volumes of liquid per pump cycle according to different operational needs. For example, when used in a cleaning system, the distance HP can be adjusted to change the volume of liquid being delivered and therefore ejected by a trocar of the cleaning system into the trocar channel. In some instances, a higher volume of fluid delivery may be selected (e.g., by increasing HP), such that more liquid is delivered, e.g., to clean a larger instrument (e.g., a larger endoscope). While in other instances, a lower volume of fluid delivery may be selected (e.g., by decreasing HP) such that less liquid is delivered, e.g., to clean a smaller instrument (e.g., smaller endoscope).

Alternatively or additionally, the fluid delivery system 510 modified by replacing a first flexible liquid channel with another (second) flexible liquid channel, where the second flexible liquid channel has different characteristics than the first flexible liquid channel. For instance, the second flexible liquid channel may be wider, thicker, less flexible, or more flexible than the first flexible liquid channel, be made from different material(s) than the first flexible liquid channel, have walls of different thickness than the walls of the first flexible liquid channel, and/or have a different cross-sectional area and/or shape than the first flexible liquid channel. Other components of the fluid delivery system 510 can also be replaced or modified, e.g., to provide for different delivery behavior.

In some cases, various adjustments of the fluid delivery system 510 may be based on the type of the instrument that is being used and/or on a type of the procedure that is being performed by an instrument. In some cases, one or more sensors (e.g., sensor(s) 232) of the surgical instrument may provide feedback to a controller of the fluid delivery system 510, such that the controller may perform certain adjustments based on that feedback. For instance, the feedback provided by the sensors may result in the controller adjusting the distance HP that the plunger 516P is depressed. Additionally, or alternatively, the adjustment may be based on a user input via a suitable user interface (e.g., a user interface associated with an I/O device 118, as shown in FIG. 1).

With the plunger 516P being depressed as shown in FIG. 5B, the pressure withing the flexible liquid channel 521 is increased to a value of PC2. The difference between the pressure PC2 and PO1 is configured to be sufficiently large, such that it is larger than the cracking pressure of the check valve 527, thereby resulting in liquid flowing from the flexible liquid channel 521 via check valve 527 towards an outflow port 529. As such, in FIG. 5B, the check valve 527 is shown as open. Further, the check valve 523 remains closed with the pressure PC2 being larger than the pressure PI1.

The plunger 516P can then be retracted or disengaged from the flexible liquid channel 521, as shown in FIG. 5C. In this stage, the flexible liquid channel 521 can revert to an uncompressed state, thereby reducing pressure to PC3. The difference between PC3 and PO1 can be smaller than the cracking pressure of valve 527 and therefore the valve 527 is closed. Further, the pressure PC3 can be less than the pressure PIT by a sufficient degree to overcome the cracking pressure of valve 523, which results in opening of the valve 523. The opening of the valve 523 can allow flow of the liquid into the flexible liquid channel 521, as shown in FIG. 5C.

Figure 7B:
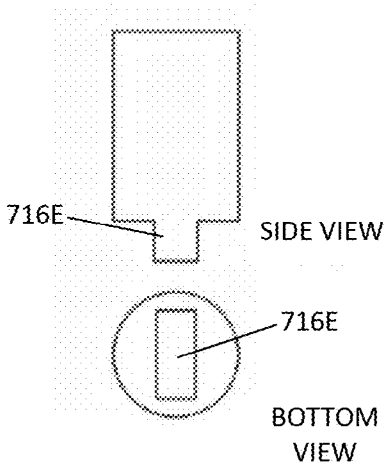
Figure 8B:
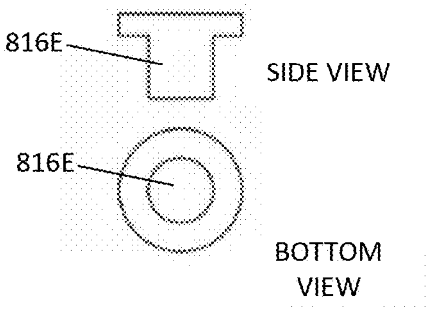
Figure 9A:
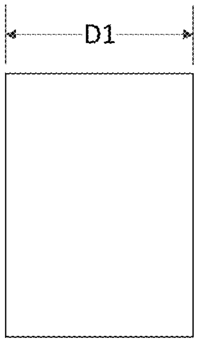
FIGS. 9A and 9B depict pump mechanisms having different widths, according to embodiments.
Figure 9B:
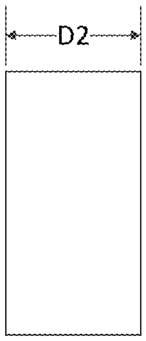

Referring now to FIG. 6A, a plot is shown that depicts a relationship between (1) a compression of a flexible liquid channel (e.g., flexible liquid channel 321, 421, 521) as measured by inches of compression and (2) a volume dispensed or delivered per pump actuation as measured in microliters (μL). For example, when the flexible liquid channel is not compressed, no volume of liquid is dispensed per pump actuation (e.g., the dispensed volume is zero), but when the flexible liquid channel is compressed by about 0.1 inches, the volume dispensed per pump actuation is about 7 μL. As shown in FIG. 6A, line 602 represents experimental data conducted using a pump mechanism implemented as a plunger having the profile as shown in FIGS. 7A and 7B, and line 604 represents the approximation of a proportional relationship between the compression amount and volume dispensed. Such data demonstrates that with appropriate selection and design of the pump mechanism, the volume of liquid being dispensed can be made proportional to the degree of compression of the liquid channel.

In operation, given the relationship between pump actuation (e.g., compression of the liquid channel) and volume dispensed, e.g., with the example shown in FIG. 6A, a fluid delivery system can be set to deliver a predetermined or fixed volume of liquid by setting the amount that a pump mechanism of the fluid delivery system compresses a flexible liquid channel. FIG. 6B describes such an operation of a fluid delivery system. For example, a process 650 can include, at 652, a controller of a fluid delivery system (e.g., controller 120, 220) receiving a user input indicating an amount of liquid to dispense. Subsequently, at 654, the controller may use the relationship between the compression amount and the volume of fluid dispensed to determine a distance that a pump mechanism (e.g., a plunger of the pump mechanism) needs to translate to deliver the volume of liquid being requested by the user.

Figure 11:
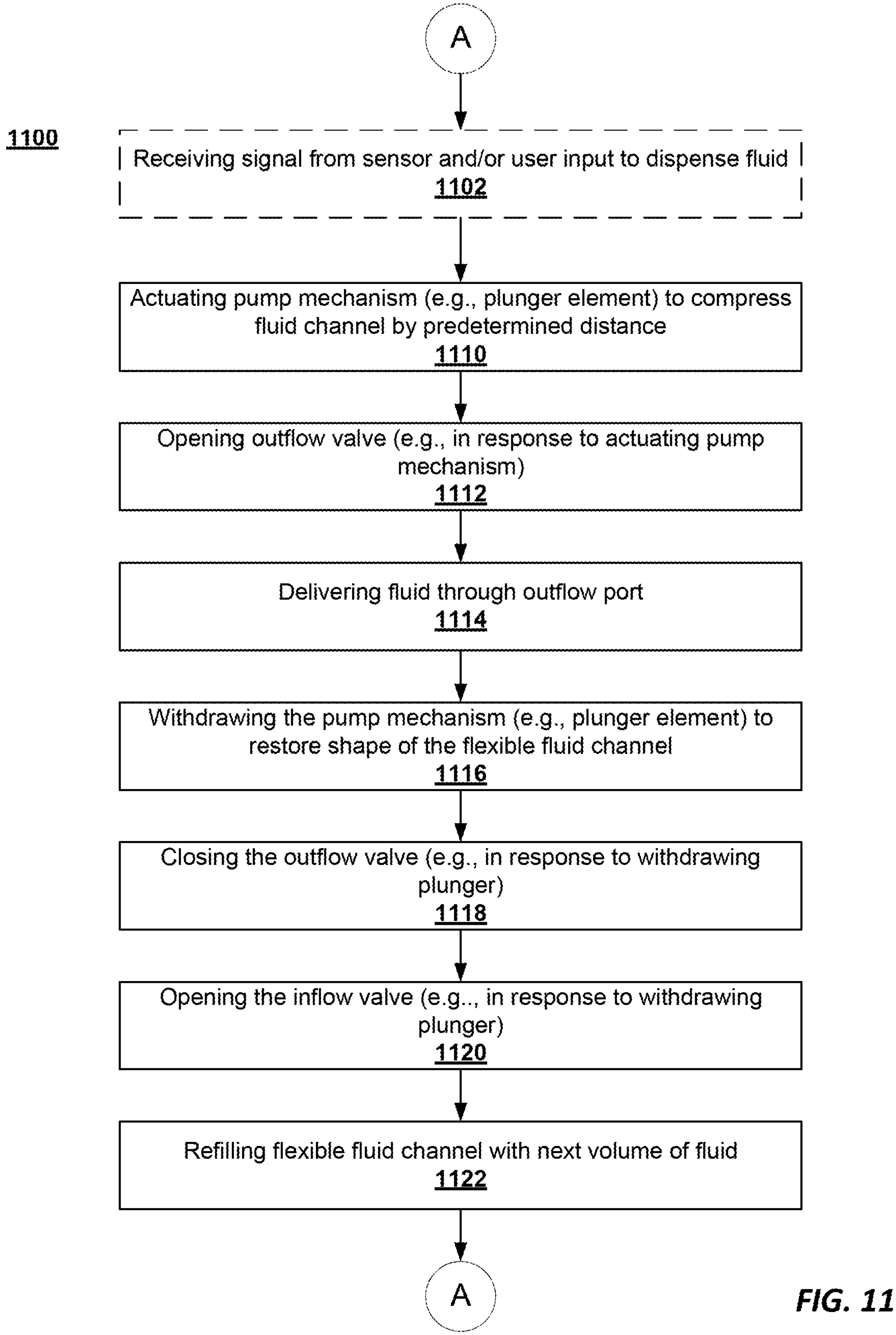
FIG. 11 is a flow chart of a method associated with the operation of a fluid delivery system, according to embodiments.

Referring now to FIG. 11, the operation of a fluid delivery system during a pump cycle is described, according to embodiments. One or more steps of the process 1100 may be performed by a controller associated with any of the fluid delivery systems described herein.

At 1102, the controller can optionally receive a signal from a sensor (e.g., sensor 232) and/or a user input to dispense a volume of fluid. For example, a sensor disposed in a surgical instrument of a cleaning system (e.g., surgical instrument 130, 230, etc.) can detect that a device has been withdrawn within the surgical instrument for cleaning. Alternatively or additionally, a sensor disposed in a liquid supply line may detect a drop in pressure and/or volume and send a signal to the controller. In response to receiving the signal from the sensor(s), the controller can actuate the pump mechanism (e.g., a plunger element) to dispense a fixed volume of fluid, at 1110. In some embodiments, the controller can receive an input from a user that instructs the controller to actuate the pump mechanism to dispense a fixed volume of fluid, at 1110. In some embodiments, the controller can automatically initiate pumping, e.g., without receiving a signal from a sensor and/or a user input. In such cases, the controller may initiate pumping in response to a wash operation being completed, based on a preset period of time, etc.

At 1110, the controller can acuate the pump mechanism (e.g., pump mechanism 316, 416, 516) to compress a fluid or liquid channel by a predetermined amount. As described with reference to FIG. 6B, the predetermined amount can be set by the controller or a user based on a calibrated relationship between volume dispensed and the compression amount. In some embodiments, the actuating of the pump mechanism includes the controller sending a signal to a pump actuator (e.g., a motor) to cause the pump mechanism to move (e.g., translate).

At 1112, in response to the compression of the flexible fluid channel, an outflow valve of the fluid delivery system (e.g., outflow valve 427, 527) can open to allow a predetermined or fixed volume of liquid to pass through the valve. For example, as described above, when the outflow valve is a check valve, the outflow valve may be opened when a fluid pressure within the flexible liquid channel is higher than the pressure downstream of the valve. Alternatively, the outflow valve may be opened via any other suitable approaches (e.g., via electrical control). At 1114, liquid can be delivered through an outflow port of the fluid delivery system (e.g., outflow port 329).

At 1116, the pump mechanism can be retracted or withdrawn to restore the shape of the flexible liquid channel. At 1118, the withdrawal of the pump mechanism may result in the closing the outflow valve. Alternatively, the outflow valve may be closed via any other suitable approaches (e.g., via electrical control). At 1120, the restoring of the shape of the flexible liquid channel can lead to an opening of an inflow valve of the fluid delivery system (e.g. inflow valve 423, 523). For example, when the inflow valve is a check valve, a pressure difference across the valve may lead to opening of the inflow valve. Alternatively, the inflow valve may be opened via any other suitable approaches (e.g., via electrical control).

At 1122, upon opening of the inflow valve, the flexible liquid channel is refilled with a next volume of fluid, e.g., supplied by a liquid reservoir and/or an external fluid source.

Figure 12:
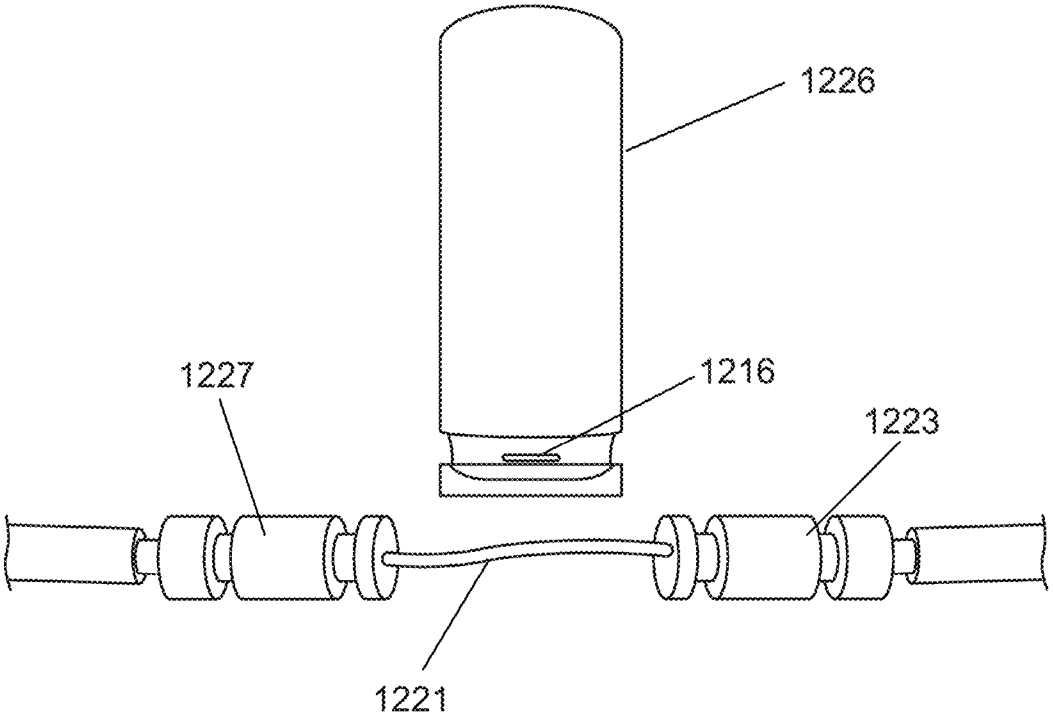
FIG. 12 depicts an example of a fluid delivery system, according to embodiments.

FIG. 12 depicts components of an example fluid delivery system, according to embodiments. The fluid delivery system can include a pump actuator 1226 that actuates a pump mechanism implemented as a pinch valve 1216. The pinch valve 1216 can define a space or passage for receiving a portion of a flexible liquid channel or tubing 1221. The flexible tubing 1221 can include two valves, i.e., an upstream or inflow valve 1223 and a downstream or outflow valve 1227. The upstream end of the flexible tubing 1221 can be coupled to a liquid reservoir, and the downstream end of the flexible tubing 1221 can be coupled to a surgical instrument or device.

In use, the flexible tubing 1221 can be positioned within the pinch valve 1216. The pinch valve 1216 can close down or compress the flexible tubing 1221 during each pump cycle. The compression of the flexible tubing 1221 can cause the opening and closing of the valves 1223, 1227, similar to the process described above with reference to FIGS. 5A-5C and 11.

The volume of the liquid that is delivered using the fluid delivery system as depicted in FIG. 12 can be impacted by multiple factors, including, for example, differential height of different parts of the liquid supply line (e.g., tubing defining path from liquid reservoir to surgical instrument), pressure being generated, valve compliance, amount of compression, flexible tubing design, etc. In some embodiments, a secondary pinch device can be incorporated into the fluid delivery system, e.g., to provide for high pressure applications.

Figure 13A:
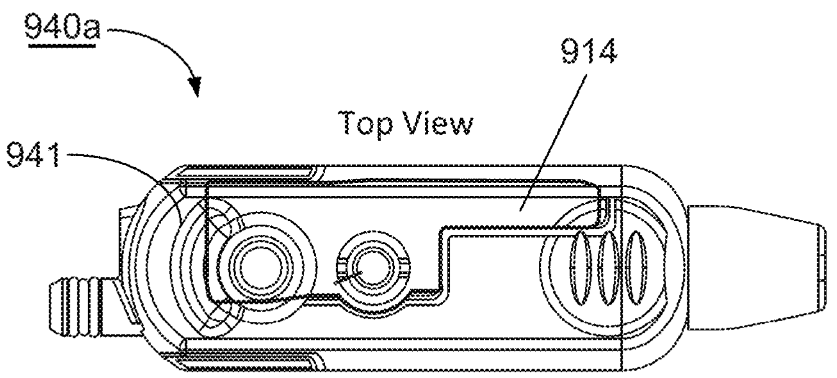
FIG. 13A-13B depict different views of a connector of a fluid delivery line, including a reservoir, according to embodiments.
Figure 13B:
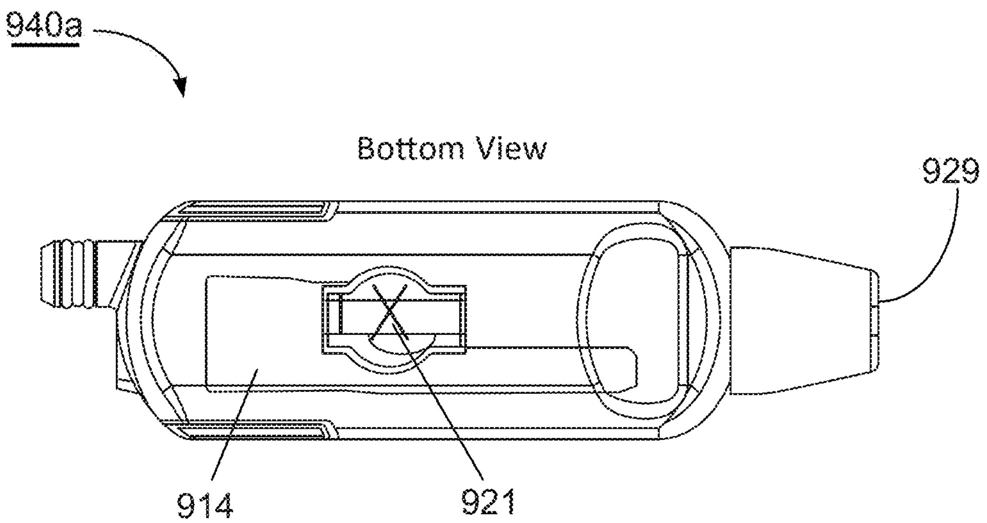

FIGS. 13A-13B depict an example of a proximal connector end or controller connection 940*a* of a fluid delivery system, according to embodiments. The proximal connector end 940*a* can be structurally and/or functionally similar to other proximal connector ends described herein, including, for example, proximal connector end 440*a*. The proximal connector end 940*a* can include a housing 941 that contains a liquid reservoir 914. In some embodiments, the liquid reservoir 914 can have a flexible design and be configured to expand when liquid is injected into the fluid reservoir 914. As such, the liquid reservoir 914 can be configured to have a bubbleless design, e.g., be moldable or expandable to allow a user to full the reservoir 914 with a liquid (e.g., a wash solution). The liquid reservoir 914 can be filled with a liquid prior to being inserted into a receptacle (e.g., receptacle 413) of a controller (e.g., a controller 120, 220) of the fluid delivery system.

The proximal connector end 940*a* can also include an outflow port 929 that is coupled downstream to a surgical instrument, as well as internal fluid channels (e.g., a flexible fluid channel 321, 421, etc.) for conveying liquid from the fluid reservoir 914 to the outflow port 929. The liquid reservoir 914 can have an opening that is fluidically coupled to the outflow port 929 but be sealed from other components of the proximal connector end 940*a*. In some embodiments, a hydrophobic filtered vent can be coupled to the liquid reservoir 914, e.g., to prevent bubbles from forming within the liquid reservoir 914. The internal fluid channels can include one or more valves, e.g., as described above with reference to FIGS. 3-5, that regulate the movement of liquid from the liquid reservoir 914 into the channels. In FIG. 13B, an "X" is placed over a spot where flexible tubing 921 of the internal fluid channels of the proximal connector end 940*a* can be compressed by a pump mechanism (e.g., pump mechanism 216, 316, etc.) to pump the liquid for delivery.

Figure 14:
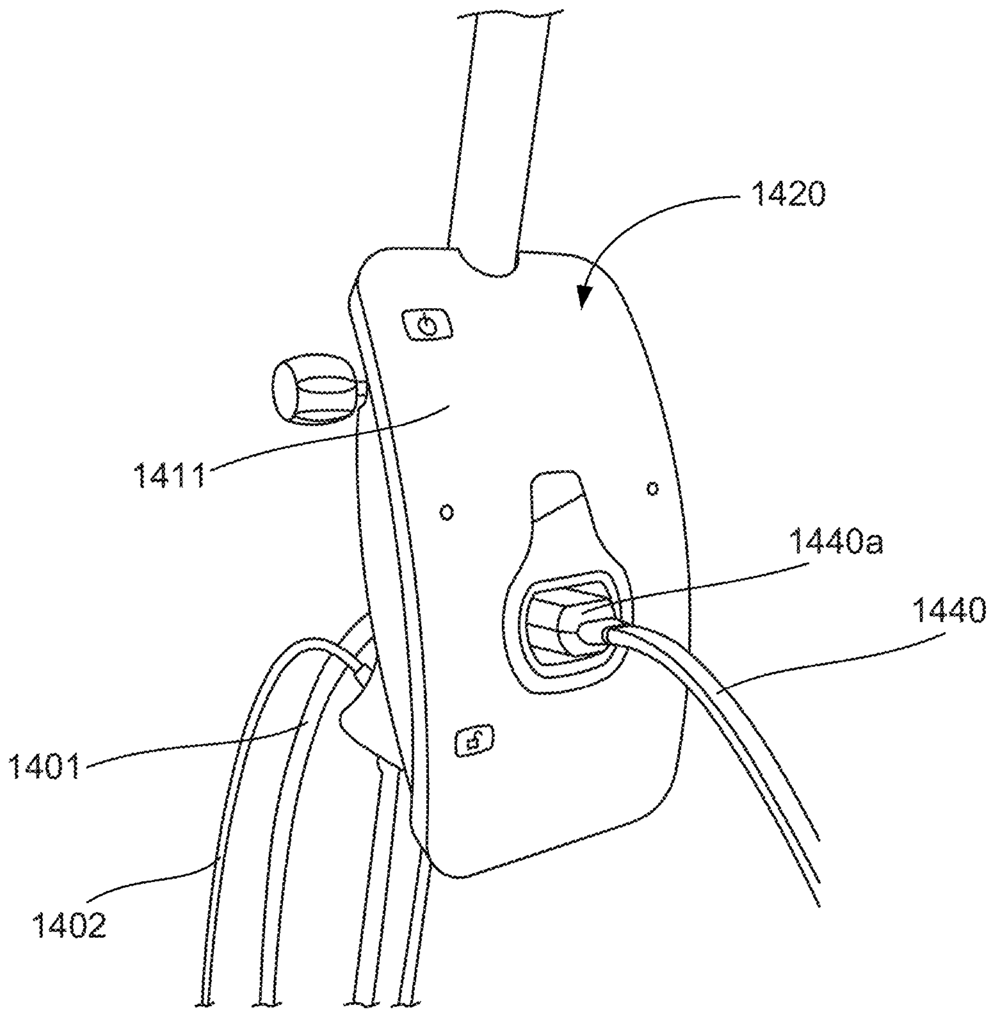
FIG. 14 depict the connections of a connector of a fluid delivery line to a fluid delivery system, according to embodiments.

FIG. 14 depicts a coupling between a proximal connector end or controller connection 1440*a* and a controller 1420 of a fluid delivery system, according to embodiments. The controller 1420 can include or be housed within a housing 1411. The housing 1411 can define a receptacle for receiving the proximal connector end 1440*a* of the connector 1440. The housing, receptacle, proximal connector end, and connector as depicted in FIG. 14 can be structurally and/or functionally similar to other housings, receptacles, proximal connector ends, and connectors described herein, including, for example, those described with reference to FIGS. 4A-4B.

The controller 1420 can control delivery of liquid and/or gas, e.g., to a surgical instrument such as a trocar. The controller 1420 can receive power via the electrical wire 1402 and gas via the gas line 1401. In some embodiments, the gas line 1401 can be configured to deliver pressurized gas including air, CO2, nitrogen, argon, or any other inert gas or combinations thereof. The proximal connector end 1440*a* can include an onboard liquid reservoir, e.g., similar to that described with reference to FIGS. 13A-13B. When the proximal connector end 1440*a* is disposed within the receptacle, the controller 1420 via a pump actuator (e.g., pump actuator 226) and pump mechanism (e.g., 216, 316, 416, etc.) can pump liquid from within the liquid reservoir to the surgical instrument.

FIGS. 15A-17B provide detailed views of a proximal connector end or controller connection 1640*a* of a connector 1640 of a fluid delivery system, according to embodiments. The proximal connector end 1640*a* can be structurally and/or functionally similar to other proximal connector ends described herein, including, for example, proximal connector ends 440*a*, 940*a*, etc. In some embodiments, the connector can be used with a cleaning system, e.g., to deliver liquid and/or gas for cleaning instruments (e.g., endoscopes) disposed within a trocar in a body lumen or cavity.

Figure 15A:
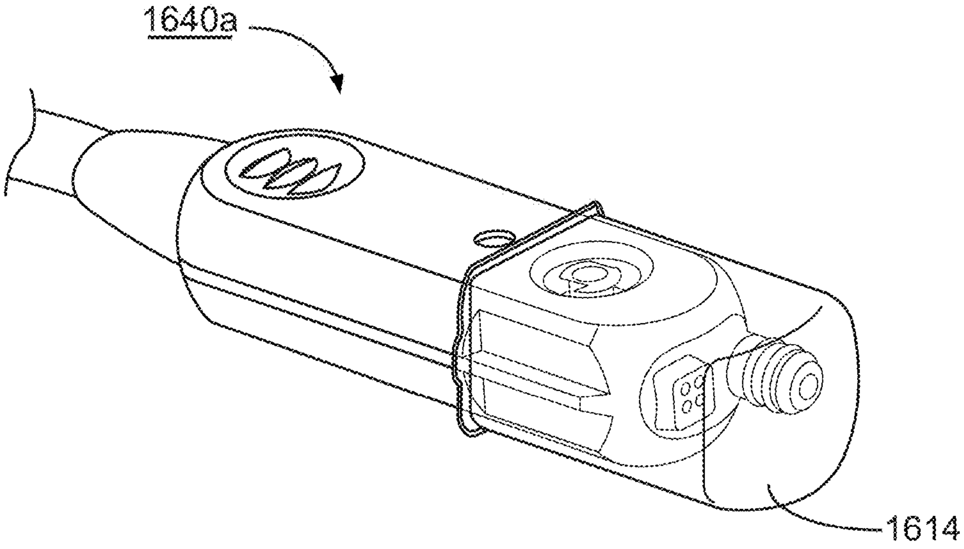
FIGS. 15A-15B depict different views of a connector of a fluid delivery line, according to embodiments.
Figure 15B:
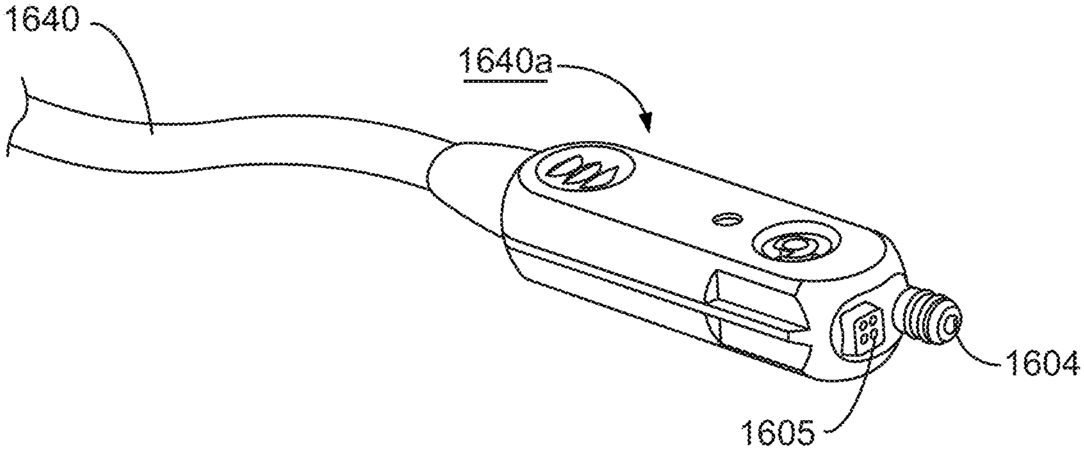

FIG. 15A depicts the proximal connector end 1640*a* prior to initial use. The proximal connector end 1640*a* may have a portion that is covered with a protective cover 1614. The protective cover 1614 can be configured to cover the portion of the proximal connector end 1640*a* that is configured for insertion into a receptacle of a controller, e.g., as described above with reference to FIG. 14. The cover 1614 can prevent that portion of the proximal connector end 1640*a* from being contaminated prior to use. The cover 1614 can be removed from the proximal connector end 1640*a*, as depicted in FIG. 15B, to expose a gas port 1604 for coupling to a gas supply line and electrical ports 1605 for receiving one or more electrical connections. When the proximal connector end 1640*a* is inserted into a controller, the gas port 1604 can be fluidically coupled to a gas source (e.g., gas source 160) and the electrical ports 1605 can be electrically coupled to one or more electrical components (e.g., power source 112, controller 120, etc.).

Figure 16:
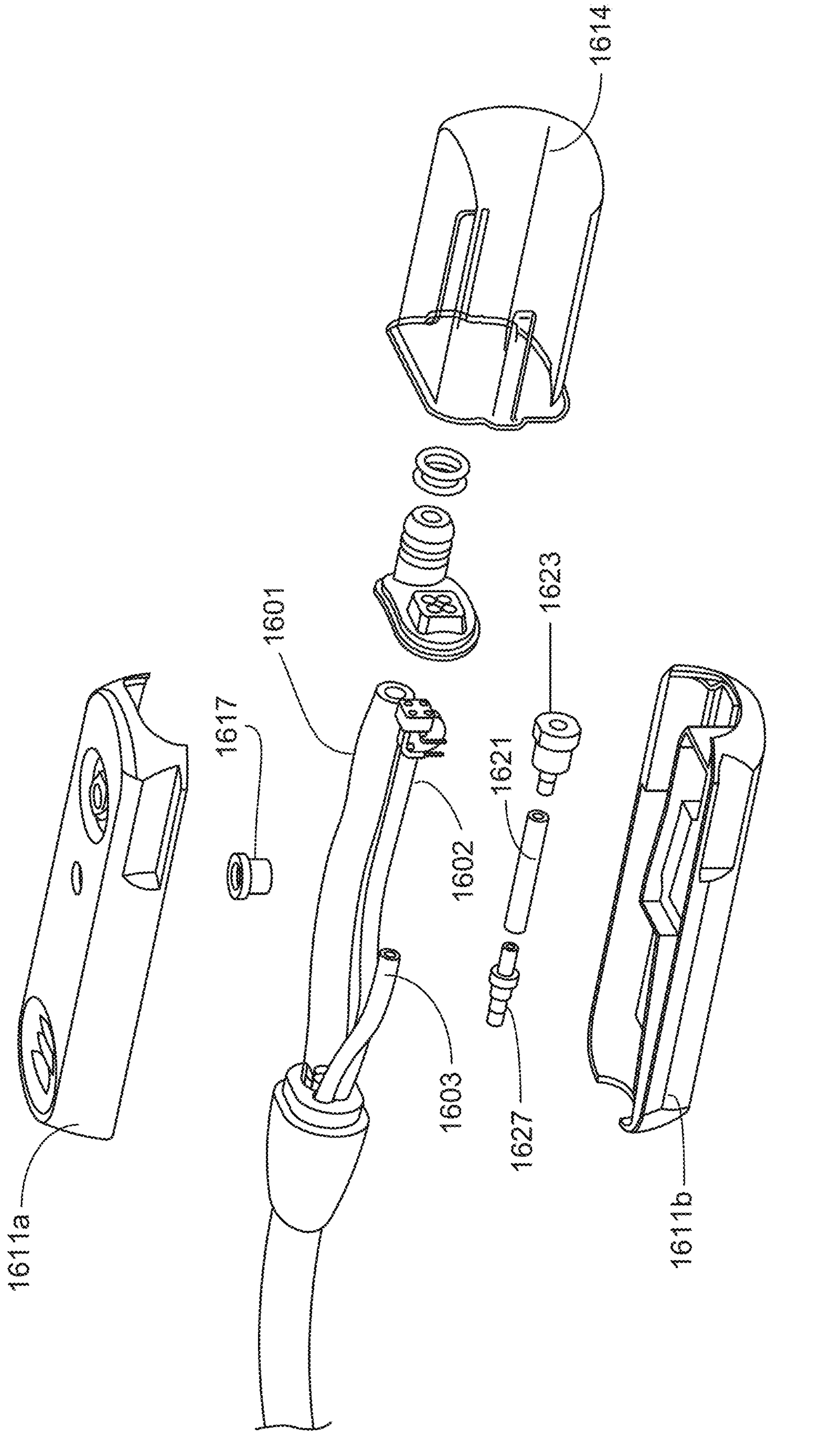
FIG. 16 depicts an exploded view of the connector of FIGS. 15A-15B.

FIG. 16 depicts an exploded view of the proximal connector end 1640*a*. The proximal connector end 1640*a* can include two housing portions 1611*a*, 1611*b* that come together to form a space for housing one or more liquid lines, gas lines, electrical lines, and/or other fluid delivery components. The liquid supply line can include an upstream or inflow valve 1623, a flexible liquid channel or tubing 1621, and a downstream or outflow valve 1627. The outflow valve 1627 can be coupled to tubing 1603 that extends through a length of the connector 1640, e.g., to provide fluid communication with a surgical instrument. The proximal connector end 1640*a* also includes a cylindrical shim 1617 (e.g., base element) that can be configured to push the flexible tubing 1621 toward a pump mechanism (not depicted) when the proximal connector end 1640*a* is coupled to the controller. The inflow valve 1623, flexible tubing 1621, outflow valve 1627, and cylindrical shim 1617 can be structurally and/or functionally similar to other like components described herein, including, for example, those described with reference to FIGS. 4A and 4B.

The gas port 1604 can be fluidically coupled to gas tubing 1601, e.g., for conveying gas through the connector 1640 to a surgical instrument. The electrical ports 1605 can be coupled to an electrical line 1602, e.g., for receiving and/or sending electrical signals to and from electrical elements on a surgical instrument. As shown, the liquid, gas, and electrical connections within the proximal connector end 1640*a* and throughout the connector 1640 can run parallel to one another (as well as the liquid reservoir, as shown in FIG. 17A), providing for easy cable management and facilitating connections between the controller, the connector 1640, and the surgical instrument.

Figure 17A:
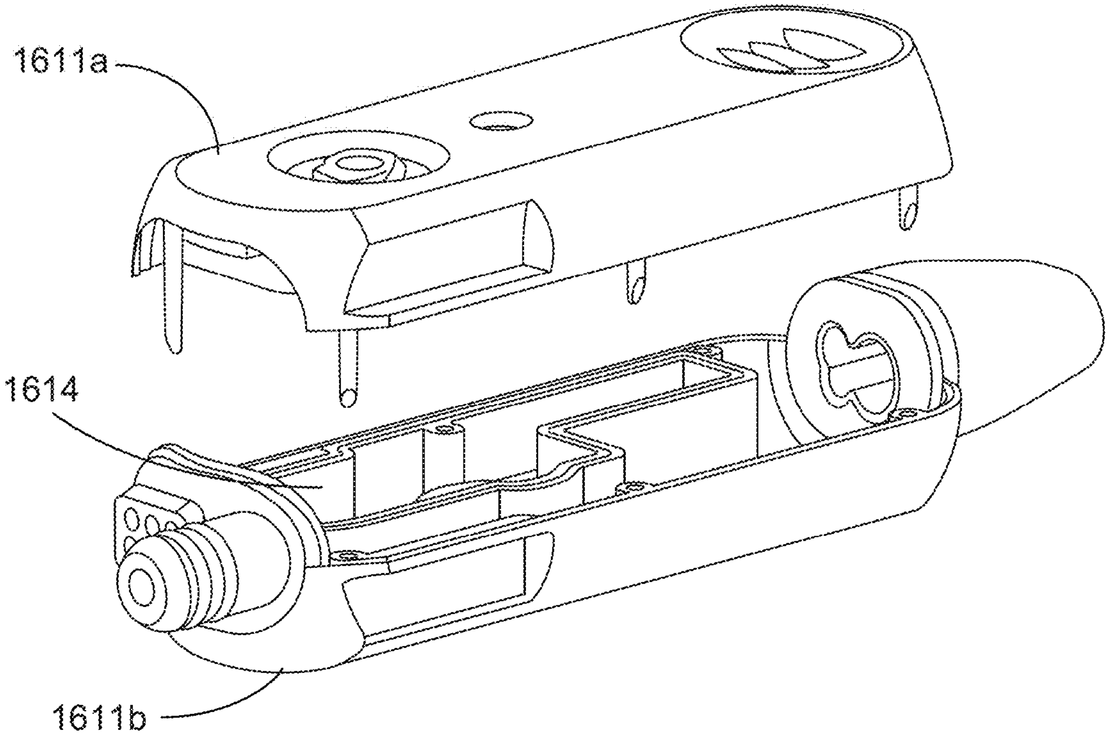
FIG. 17A depicts a view of the connector of FIGS. 15A-15B with an outer housing being open to show an internal space for receiving a fluid reservoir.
Figure 17B:
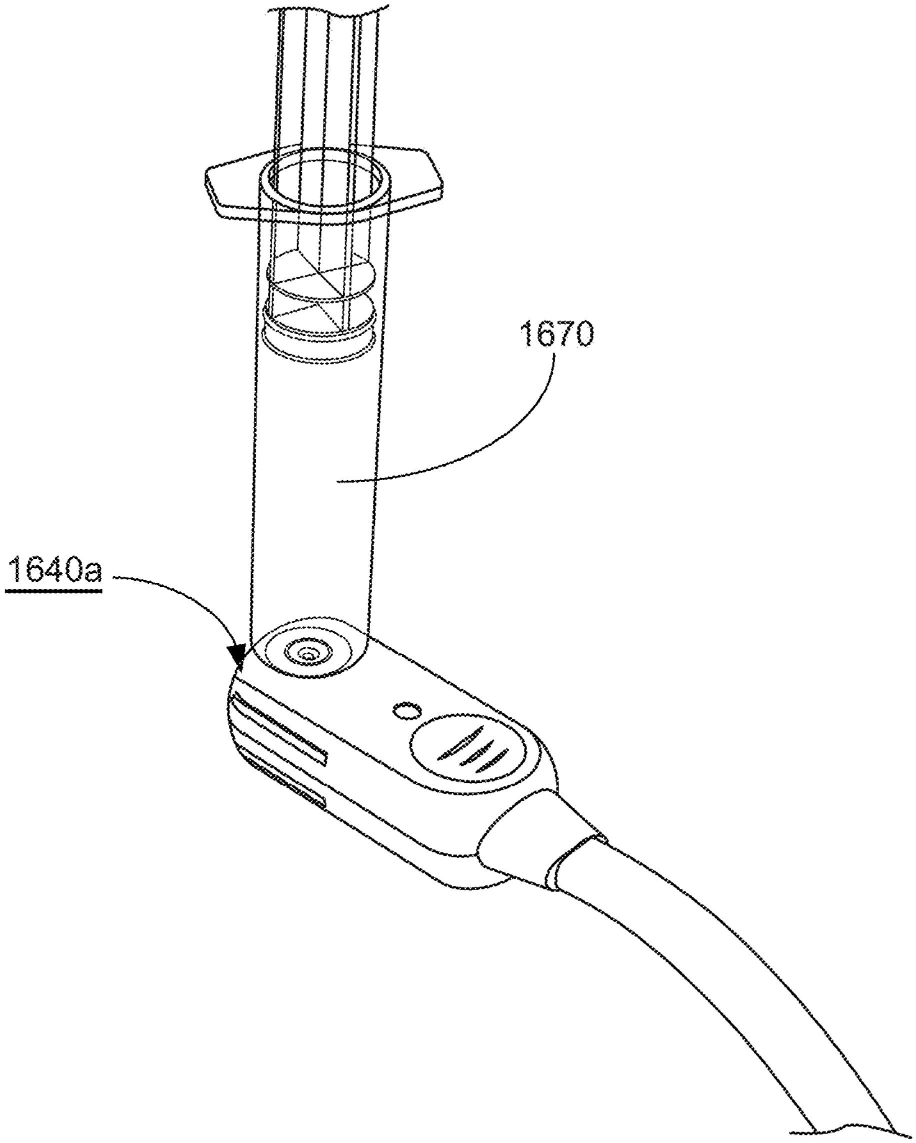
FIG. 17B depicts pre-filling of a fluid reservoir of a fluid delivery device, according to embodiments.

FIG. 17A depicts an open view of the proximal connector end 1640*a*, showing a space 1614 for receiving a liquid reservoir. The space 1614 can generally approximate the size and/or geometry of the liquid reservoir. In use, a liquid reservoir disposed within the space 1614 can be configured to expand within the space 1614 as it is filled with a liquid. FIG. 17B depicts a liquid filing operation, whereby an external liquid source 1670 implemented as a syringe is used to fill the fluid reservoir with a predetermined amount of liquid. As described above, this predetermined amount of liquid can be sufficient for providing liquid volumes for multiple pump cycles (e.g., for one or more wash operations).

Figure 18A:
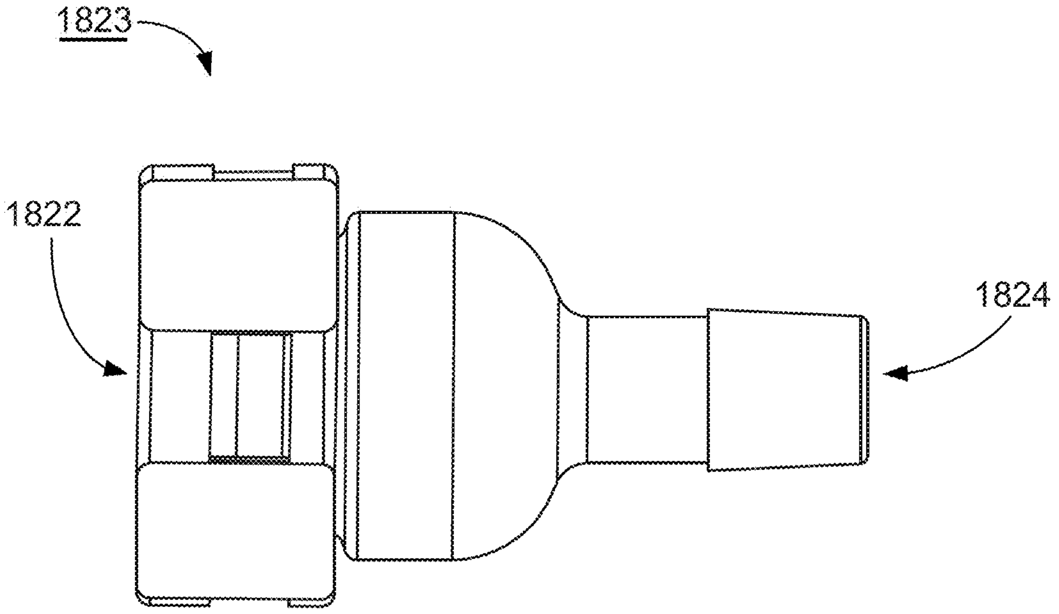
FIGS. 18A-18B depict a valve of a fluid delivery device, according to embodiments.
Figure 18B:
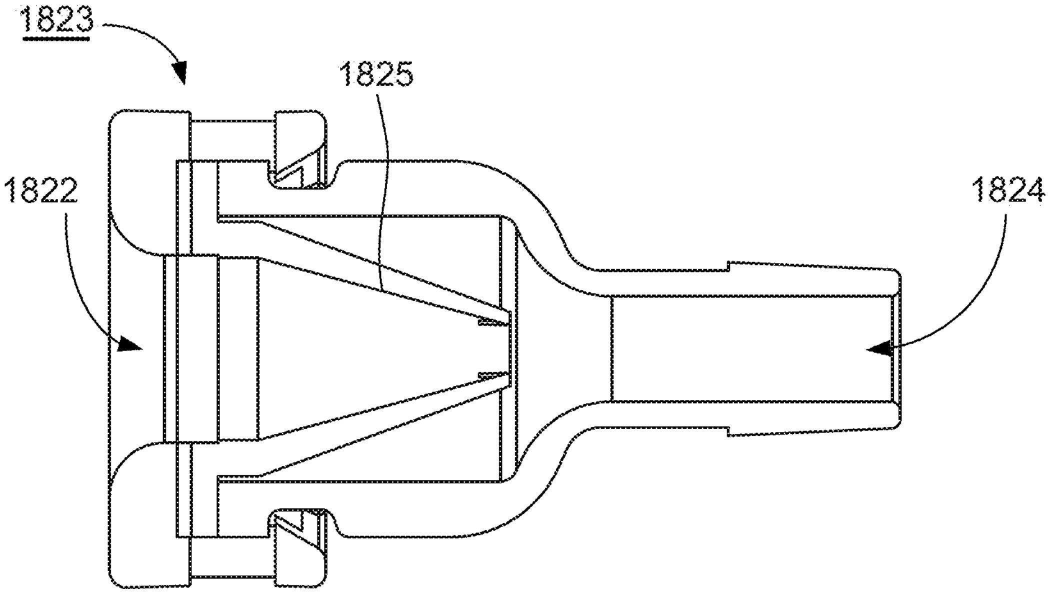

FIGS. 18A-18B provide a detailed view of an upstream or inflow valve 1823 of a fluid delivery system, according to embodiments. The upstream valve 1823 can be structurally and/or functionally similar to other upstream valves described herein, including, for example, upstream valve 1623. The upstream valve 1823 can include a inlet 1822 and an outlet 1824 with a duckbill valve 1825 disposed between the inlet 1822 and the outlet 1824. The valve 1823 can be configured to open in response to a pressure differential between its inlet and outlet, e.g., a lower pressure at the outlet vs. the inlet due to the flexible liquid tube reverting to its uncompressed state can open the valve 1823.

Figure 19A:
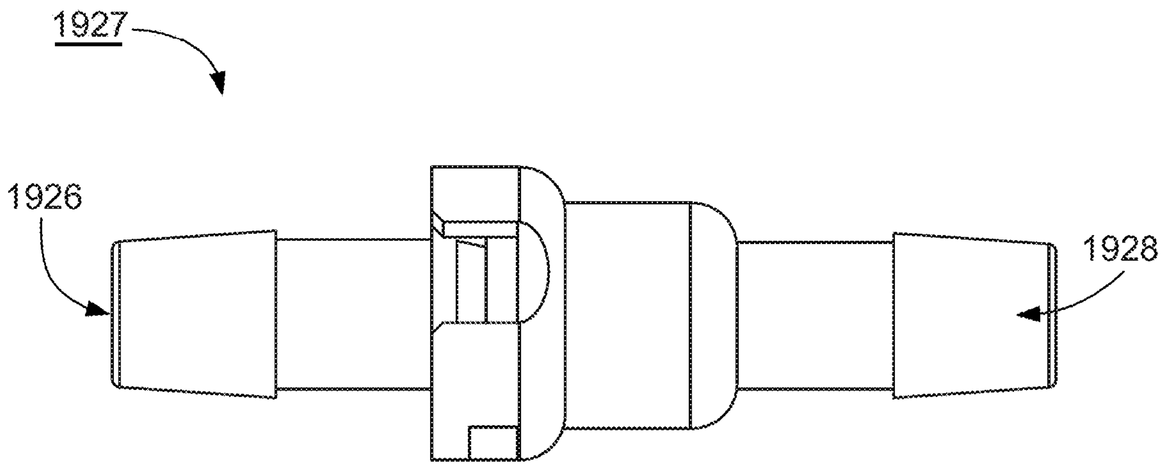
FIGS. 19A-19B depict a valve of a fluid delivery device, according to embodiments.
Figure 19B:
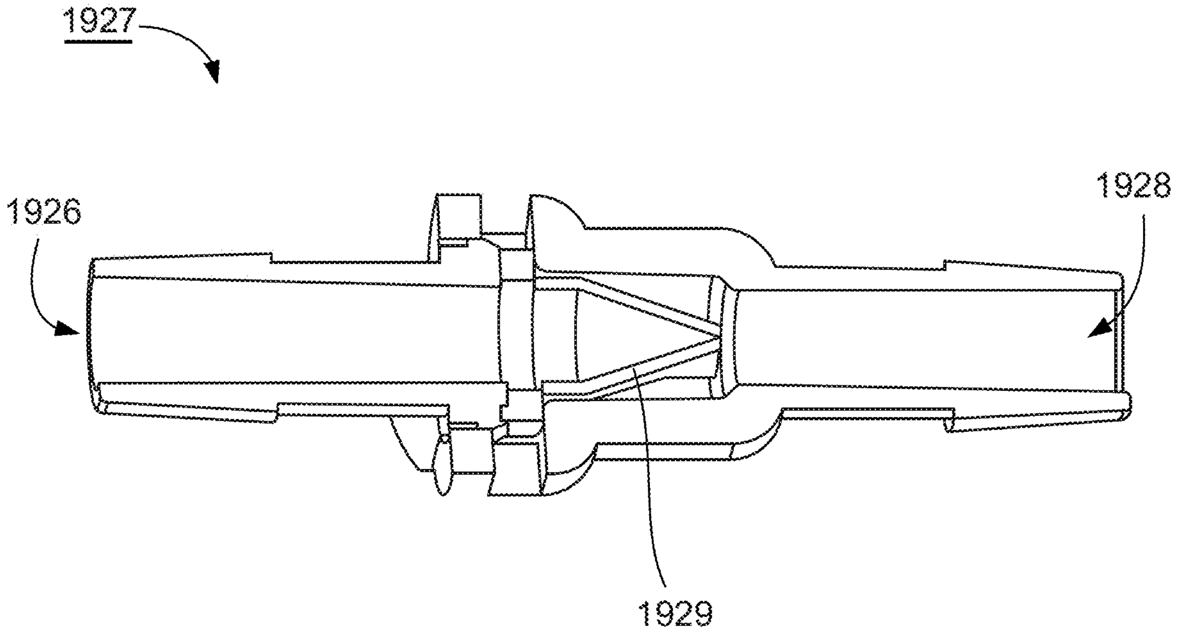

FIGS. 19A-19B provide a detailed view of a downstream or outflow valve 1927 of a fluid delivery system, according to embodiments. The downstream valve 1927 can be structurally and/or functionally similar to other downstream valves described herein, including, for example, downstream valve 1627. The downstream valve 1927 can include a inlet 1926 and an outlet 1928 with a duckbill valve 1929 disposed between the inlet 1926 and the outlet 1928. The valve 1927 can be configured to open in response to a pressure differential between its inlet and outlet, e.g., a greater pressure at the inlet vs. the outlet due to the compression of the flexible liquid tube can open the valve 1927. In some embodiments, the downstream valve 1927 can be configured to open in response to lower pressures than an upstream valve, such as, for example, upstream valve 1823. As such, the downstream valve 1927 can have smaller dimensions than those of the upstream valve.

Figure 20:
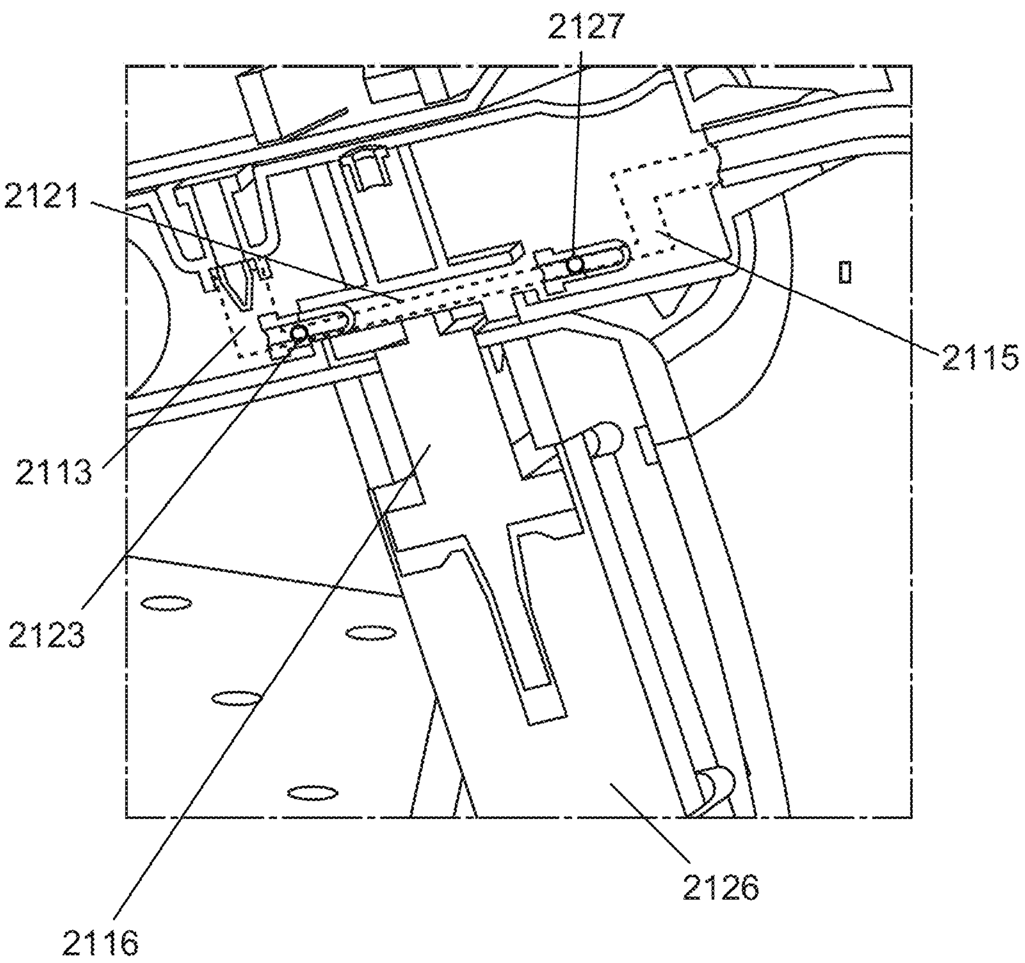
FIG. 20 provides a detailed view of internal connections within a connector of a fluid delivery line, according to embodiments.

FIG. 20 provides a detailed view of the inner connections between a liquid reservoir and the liquid channels within a proximal connector end of a fluid delivery system, according to embodiments. Such connections can be structurally and/or functionally similar to those described with reference to other embodiments disclosed herein, including, for example, those described with reference to FIGS. 15A-17B.

As depicted in FIG. 20, a first liquid channel 2113 can extend from a valved connection to a liquid reservoir to an upstream valve 2123. A second liquid channel 2121 then extends between the upstream valve 2123 and a downstream valve 2127. A third liquid channel 2115 then extends between the downstream valve 2127 and an outlet path out of the proximal connector end. It can be appreciated that the liquid channels 2113, 2121, 2115 are schematically depicted in FIG. 20 for illustrative purposes, and that the actual structure of such channels are not depicted. The upstream valve 2123, liquid channel 2121, and downstream valve 2127 can be structurally and/or functionally similar to other upstream valves, liquid channels, and downstream valves described herein, respectively, including, for example, those described with reference to FIGS. 15A-19B. As such, further details of such components are not provided herein again.

As depicted in FIG. 20, the proximal connector end is disposed within a receptacle of a controller of a fluid delivery system. In such position, a pump mechanism 2116 can be configured to engage with the flexible tubing 2121, e.g., to compress the tubing 2121 and delivery fixed volumes of liquid. The pump mechanism 2116 can be coupled to a portion of a pump actuator 2126, e.g., including an electric motor or other actuation mechanism for driving the movement of the pump mechanism 2116.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used in this specification, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

The term "substantially" when used in connection with "cylindrical," "linear," and/or other geometric relationships is intended to convey that the structure so defined is nominally cylindrical, linear or the like. As one example, a portion of a support member that is described as being "substantially linear" is intended to convey that, although linearity of the portion is desirable, some non-linearity can occur in a "substantially linear" portion. Such non-linearity can result from manufacturing tolerances, or other practical considerations (such as, for example, the pressure or force applied to the support member). Thus, a geometric construction modified by the term "substantially" includes such geometric properties within a tolerance of plus or minus 5% of the stated geometric construction. For example, a "substantially linear" portion is a portion that defines an axis or center line that is within plus or minus 5% of being linear.

As used herein, the term "set" and "plurality" can refer to multiple features or a singular feature with multiple parts. For example, when referring to a set of devices, the set of devices can be considered as one device with multiple portions, or the set of devices can be considered as multiple, distinct devices. Thus, a set of portions or a plurality of portions may include multiple portions that are either continuous or discontinuous from each other. A plurality of particles or a plurality of materials can also be fabricated from multiple items that are produced separately and are later joined together (e.g., via mixing, an adhesive, or any suitable method).

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. An apparatus, comprising:
- a first housing;
- a liquid reservoir disposed within the first housing;
- a liquid outlet configured to couple to an instrument;
- a liquid supply line disposed in the first housing, the liquid supply line being fluidically coupled to the liquid reservoir and to the liquid outlet, the liquid supply line having at least one portion that is flexible;
- first and second valves disposed along the liquid supply line, the first valve being disposed upstream of the at least one flexible portion and the second valve being disposed downstream of the at least one flexible portion,
- the at least one flexible portion being compressible to pump liquid disposed within the liquid supply line toward the liquid outlet,
- a second housing defining a receptacle for receiving at least a portion of the first housing; and
- a pump mechanism at least partially disposed within the second housing and configured to extend out of the second housing toward the first housing, the pump mechanism configured to be actuated to compress the at least one flexible portion of the liquid supply line when the first housing is received within the receptacle of the second housing.

2. The apparatus of claim 1, further comprising a gas supply line having at least a portion disposed within the first housing, the gas supply line being configured to couple a gas source disposed outside of the first housing to the instrument.

3. The apparatus of claim 1, further comprising an electrical line having at least a portion disposed within the first housing, the electrical line being configured to couple a processor to the instrument.

4. The apparatus of claim 1, wherein the pump mechanism includes a plunger, the plunger having a rectangular slot for contacting the at least one flexible portion of the liquid supply line.

5. The apparatus of claim 1, wherein the liquid outlet is configured to supply a fixed volume of liquid in response to the compression of the at least one flexible portion of the liquid supply line, the fixed volume of liquid being less than about 20 μL.

6. An apparatus, comprising:
- a first housing;
- an inflow port couplable to a liquid reservoir, the liquid reservoir disposed within the first housing;
- an outflow port couplable to an instrument;
- a flexible liquid channel disposed within the first housing and coupled to the inflow port and the outflow port, the flexible liquid channel configured to be compressed such that liquid within the flexible liquid channel is displaced toward the outflow port;
- an inflow valve disposed upstream of the flexible liquid channel;

an outflow valve disposed downstream of the flexible liquid channel, the outflow valve configured to open, when the flexible liquid channel is compressed, such that a first volume of liquid can pass through the outflow valve toward the outflow port, and the outflow valve configured to close and the inflow valve configured to open, when the flexible liquid channel transitions back to an uncompressed state after being compressed, such that a second volume of liquid can pass through the inflow valve and into the flexible liquid channel, a second housing defining a receptacle for receiving at least a portion of the first housing; and a pump mechanism at least partially disposed within the second housing and configured to extend out of the second housing toward the first housing, the pump mechanism configured to be actuated to compress at least a portion of the flexible liquid channel when the first housing is received within the receptacle of the second housing.

7. The apparatus of claim 6, wherein the outflow valve and the inflow valve are one-way check valves.

8. The apparatus of claim 6, wherein the outflow valve is configured to open in response to a first pressure difference between an inlet of the outflow valve and an outlet of the outflow valve, and the inflow valve is configured to open in response to a second pressure difference between an inlet of the inflow valve and an outlet of the inflow valve, the first pressure difference being greater than the second pressure difference.

9. The apparatus of claim 6, wherein the first and second volumes of liquid are less than about 20 μL.

10. The apparatus of claim 6, wherein the pump mechanism includes a plunger, the plunger having a rectangular slot for contacting at least one portion of the flexible liquid channel.

11. An apparatus, comprising:

a first housing;

a liquid supply line disposed within the first housing, the liquid supply line including a liquid inlet that is fluidically coupled to a liquid reservoir disposed within the first housing and a liquid outlet that is fluidically coupled to an instrument, the liquid supply line having at least one portion that is configured to be compressed to pump liquid disposed within the liquid supply line toward the instrument;

a second housing defining a receptacle for receiving at least a portion of the first housing;

a pump mechanism at least partially disposed within the second housing and configured to extend out of the second housing toward the first housing, the pump mechanism configured to be actuated to compress the at least one portion of the liquid supply line when the first housing is received within the receptacle of the second housing; and a controller operatively coupled to the pump mechanism and to the instrument, the controller configured to:

receive a signal from a sensor disposed at the instrument indicating that a device is positioned for cleaning relative to the instrument;

in response to receiving the signal from the sensor, activating a wash sequence in which a first volume of liquid is delivered into the instrument to clean the device; and activating the pump mechanism to compress the at least one portion of the liquid supply line to pump a second volume of liquid toward the instrument such that the instrument is primed for a subsequent wash sequence.

12. The apparatus of claim 11, further comprising:

a gas supply line configured to deliver gas to the instrument; and a gas control valve configured to control the delivery of the gas, the controller configured to activate the wash sequence by controlling the gas control valve to deliver the gas to propel the first volume of liquid into the instrument.

13. The apparatus of claim 12, further comprising an electrical line configured to couple the sensor to the controller.

14. The apparatus of claim 13, further comprising a cable housing that houses at least a portion of the liquid supply line, the gas supply line, and the electrical line.

15. The apparatus of claim 14, wherein the cable housing includes a first end that is couplable to the controller and a second end that is couplable to the instrument.

16. The apparatus of claim 11, wherein the first and second volumes of liquid are less than about 20 μL.

17. The apparatus of claim 11, further comprising first and second valves disposed along the liquid supply line, the first valve being disposed upstream of the at least one portion and the second valve being disposed downstream of the at least one portion.

18. The apparatus of claim 11, wherein the pump mechanism includes a plunger, the plunger having a rectangular slot for contacting the at least one portion of the liquid supply line.

* * * * *